(12) United States Patent
Brown

(10) Patent No.: US 9,120,919 B2
(45) Date of Patent: Sep. 1, 2015

(54) TUNABLE SEGMENTED POLYACETAL

(75) Inventor: Malcolm Brown, Heslington (GB)

(73) Assignee: Smith & Nephew, Inc., Memphis, TN (US)

(*) Notice: Subject to any disclaimer, the term of this patent is extended or adjusted under 35 U.S.C. 154(b) by 2243 days.

(21) Appl. No.: 10/584,115

(22) PCT Filed: Dec. 22, 2004

(86) PCT No.: PCT/GB2004/005445
§ 371 (c)(1),
(2), (4) Date: Aug. 6, 2007

(87) PCT Pub. No.: WO2005/061617
PCT Pub. Date: Jul. 7, 2005

(65) Prior Publication Data
US 2007/0299156 A1    Dec. 27, 2007

(30) Foreign Application Priority Data
Dec. 23, 2003 (GB) .................................. 0329654.8

(51) Int. Cl.
*C08G 81/00* (2006.01)
*C08L 101/16* (2006.01)
*A61L 27/18* (2006.01)
*A61L 27/58* (2006.01)
*C08G 63/664* (2006.01)
(Continued)

(52) U.S. Cl.
CPC ............... *C08L 101/16* (2013.01); *A61L 27/18* (2013.01); *A61L 27/58* (2013.01); *C08G 63/664* (2013.01); *C08G 63/668* (2013.01); *C08L 59/00* (2013.01); *A61L 2400/06* (2013.01); *C08G 81/024* (2013.01); *C08G 81/027* (2013.01); *C08G 81/028* (2013.01); *C08G 2261/126* (2013.01); *C08K 3/32* (2013.01)

(58) Field of Classification Search
CPC .... C08G 81/024; C08G 81/02; C08G 81/025; C08G 81/027; C08G 81/028; C08G 65/34; C08L 2203/02
USPC ...................... 523/114; 525/469, 79; 528/392
See application file for complete search history.

(56) References Cited

U.S. PATENT DOCUMENTS 3,531,561 A    9/1970    Trebu
3,636,956 A    1/1972    Schneider
(Continued)

FOREIGN PATENT DOCUMENTS

CA    2254002    5/2000
CN    1857742 A    11/2006
(Continued)

OTHER PUBLICATIONS

Grijpma, D.W., et al., 'Chain Entanglement, Mechanical Properties and Drawability of Poly (Lactide),' Colloid Polym Sci., 272: 1068-1081 (1994).
(Continued)

*Primary Examiner* — Michael Pepitone
(74) *Attorney, Agent, or Firm* — David L. Fox; JL Salazar Law Firm

(57) ABSTRACT

The present invention relates to polymer compositions namely biodegradable segmented block copolymers comprising polyol residues having a number average molecular weight of at least 4000 Daltons and in that the polyols are connected by actual linkages.

30 Claims, 6 Drawing Sheets

(51) Int. Cl.
  *C08G 63/668* (2006.01)
  *C08L 59/00* (2006.01)
  C08G 81/02 (2006.01)
  C08K 3/32 (2006.01)

(56) References Cited

U.S. PATENT DOCUMENTS

| | | |
|---|---|---|
| 3,736,646 A | 6/1973 | Schmitt |
| 3,797,499 A | 3/1974 | Schneider |
| 4,137,921 A | 2/1979 | Okuzumi |
| 4,181,983 A | 1/1980 | Kulkarni |
| 4,438,253 A | 3/1984 | Casey et al. |
| 4,523,591 A | 6/1985 | Kaplan |
| 4,539,981 A | 9/1985 | Tung |
| 4,549,010 A * | 10/1985 | Sparer et al. ............ 528/361 |
| 4,559,945 A | 12/1985 | Koelmel et al. |
| 4,636,215 A | 1/1987 | Schwartz |
| 4,700,704 A | 10/1987 | Jamiolkowski et al. |
| 4,756,307 A | 7/1988 | Crowninshield |
| 4,776,329 A | 10/1988 | Treharne |
| 4,840,632 A | 6/1989 | Kampner |
| 4,858,603 A | 8/1989 | Clemow et al. |
| 4,916,207 A | 4/1990 | Boyle, Jr. et al. |
| 4,938,763 A | 7/1990 | Dunn et al. |
| 4,950,258 A | 8/1990 | Kawai et al. |
| 4,968,317 A | 11/1990 | Tormala et al. |
| 4,990,161 A | 2/1991 | Kampner |
| 5,049,591 A | 9/1991 | Hayashi et al. |
| 5,053,035 A | 10/1991 | McLaren |
| 5,108,755 A * | 4/1992 | Daniels et al. ............ 424/426 |
| 5,110,852 A | 5/1992 | Gogolewski et al. |
| 5,192,301 A | 3/1993 | Kamika |
| 5,201,738 A | 4/1993 | Scott et al. |
| 5,201,771 A | 4/1993 | Belykh et al. |
| 5,250,584 A | 10/1993 | Ikada et al. |
| 5,266,608 A | 11/1993 | Katz et al. |
| 5,275,601 A | 1/1994 | Gogolewski et al. |
| 5,294,395 A | 3/1994 | Broyer |
| 5,333,624 A | 8/1994 | Tovey |
| 5,360,448 A | 11/1994 | Thramann |
| 5,364,400 A | 11/1994 | Rego, Jr. et al. |
| 5,376,120 A | 12/1994 | Sarver et al. |
| 5,383,931 A | 1/1995 | Hehli et al. |
| 5,407,445 A | 4/1995 | Tautvydas et al. |
| 5,417,712 A | 5/1995 | Whittaker |
| 5,437,918 A | 8/1995 | Taniguchi |
| 5,441,515 A | 8/1995 | Khosravi |
| 5,458,653 A | 10/1995 | Davidson |
| 5,470,334 A | 11/1995 | Ross et al. |
| 5,522,817 A | 6/1996 | Sander et al. |
| 5,525,706 A | 6/1996 | Gruber et al. |
| 5,527,337 A | 6/1996 | Stack et al. |
| 5,527,341 A | 6/1996 | Gogolewski et al. |
| 5,562,704 A | 10/1996 | Tamminmaki et al. |
| 5,569,250 A | 10/1996 | Sarver et al. |
| 5,571,193 A | 11/1996 | Kampner |
| 5,571,204 A | 11/1996 | Nies |
| 5,633,002 A | 5/1997 | Stricker |
| 5,634,936 A | 6/1997 | Linden |
| 5,641,502 A | 6/1997 | Skalla et al. |
| 5,660,846 A | 8/1997 | Cheikh |
| 5,665,831 A | 9/1997 | Neuenschwander et al. |
| 5,670,161 A | 9/1997 | Healy |
| 5,676,699 A | 10/1997 | Gogolewski et al. |
| 5,690,671 A | 11/1997 | McGurk |
| 5,695,497 A | 12/1997 | Stahelin |
| 5,700,901 A | 12/1997 | Hurst et al. |
| 5,716,410 A | 2/1998 | Wang et al. |
| 5,716,413 A | 2/1998 | Walter et al. |
| 5,733,330 A | 3/1998 | Cox |
| 5,741,329 A | 4/1998 | Agrawal et al. |
| 5,760,118 A | 6/1998 | Sinclair |
| 5,766,239 A | 6/1998 | Cox |
| 5,766,618 A | 6/1998 | Laurencin et al. |
| 5,792,400 A | 8/1998 | Talja et al. |
| 5,817,328 A | 10/1998 | Gresser et al. |
| 5,834,582 A | 11/1998 | Sinclair |
| 5,837,276 A | 11/1998 | Cheikh |
| 5,853,639 A | 12/1998 | Kawakami et al. |
| 5,863,297 A | 1/1999 | Walter et al. |
| 5,868,746 A | 2/1999 | Sarver et al. |
| 5,893,850 A | 4/1999 | Cachia |
| 5,902,599 A | 5/1999 | Anseth et al. |
| 5,904,658 A | 5/1999 | Niederauer et al. |
| 5,908,918 A | 6/1999 | Chen |
| 5,935,172 A | 8/1999 | Ochoa et al. |
| 5,939,453 A * | 8/1999 | Heller et al. ............ 514/452 |
| 5,947,893 A | 9/1999 | Agrawal et al. |
| 5,968,092 A | 10/1999 | Buscemi |
| 5,977,204 A | 11/1999 | Boyan et al. |
| 5,980,564 A | 11/1999 | Stinson |
| 5,997,580 A | 12/1999 | Mastrorio et al. |
| 5,997,582 A | 12/1999 | Weiss |
| 6,001,100 A | 12/1999 | Sherman et al. |
| 6,001,101 A | 12/1999 | Augagneur et al. |
| 6,005,161 A | 12/1999 | Brekke et al. |
| 6,013,080 A | 1/2000 | Khalili |
| 6,022,352 A | 2/2000 | Vandewalle |
| 6,071,312 A | 6/2000 | Lampe et al. |
| 6,071,982 A | 6/2000 | Wise et al. |
| 6,077,989 A | 6/2000 | Kandel et al. |
| 6,113,624 A | 9/2000 | Bezwada et al. |
| 6,136,369 A | 10/2000 | Leitao et al. |
| 6,150,497 A | 11/2000 | Sastry et al. |
| 6,156,842 A | 12/2000 | Hoenig et al. |
| 6,160,084 A | 12/2000 | Langer et al. |
| 6,162,225 A | 12/2000 | Gertzman et al. |
| 6,168,570 B1 | 1/2001 | Ferrera |
| 6,179,842 B1 | 1/2001 | Spotorno et al. |
| 6,187,008 B1 | 2/2001 | Hamman |
| 6,203,573 B1 | 3/2001 | Walter et al. |
| 6,206,883 B1 | 3/2001 | Tunc |
| 6,248,108 B1 | 6/2001 | Tormala |
| 6,248,430 B1 | 6/2001 | Toyoda et al. |
| 6,281,262 B1 | 8/2001 | Shikinami |
| 6,283,973 B1 | 9/2001 | Hubbard et al. |
| 6,293,950 B1 | 9/2001 | Lynch et al. |
| 6,299,448 B1 | 10/2001 | Zdrahala et al. |
| 6,303,697 B1 | 10/2001 | Yuan et al. |
| 6,315,788 B1 | 11/2001 | Roby |
| 6,344,496 B1 | 2/2002 | Niederauer et al. |
| 6,375,465 B1 | 4/2002 | Engman et al. |
| 6,388,043 B1 | 5/2002 | Langer et al. |
| 6,423,062 B2 | 7/2002 | Enayati |
| 6,425,923 B1 | 7/2002 | Stalcup et al. |
| 6,436,136 B1 | 8/2002 | Flodin et al. |
| 6,447,515 B1 | 9/2002 | Meldrum |
| 6,468,277 B1 | 10/2002 | Justin et al. |
| 6,471,707 B1 | 10/2002 | Miller et al. |
| 6,486,296 B1 | 11/2002 | Shimamoto et al. |
| 6,503,278 B1 | 1/2003 | Pohjonen |
| 6,503,991 B2 | 1/2003 | Shalaby |
| 6,511,511 B1 | 1/2003 | Slivka et al. |
| 6,514,286 B1 | 2/2003 | Leatherbury et al. |
| 6,547,792 B1 | 4/2003 | Tsuji et al. |
| 6,565,606 B1 | 5/2003 | Bruce et al. |
| 6,579,533 B1 | 6/2003 | Tormala et al. |
| 6,599,323 B2 | 7/2003 | Melican et al. |
| 6,605,090 B1 | 8/2003 | Trieu et al. |
| 6,613,089 B1 | 9/2003 | Estes et al. |
| 6,623,487 B1 | 9/2003 | Goshert |
| 6,652,582 B1 | 11/2003 | Stinson |
| 6,716,957 B2 | 4/2004 | Tunc |
| 6,719,935 B2 | 4/2004 | Tunc |
| 6,720,402 B2 | 4/2004 | Langer et al. |
| 6,726,696 B1 | 4/2004 | Houser et al. |
| 6,758,862 B2 | 7/2004 | Berry et al. |
| 6,758,863 B2 | 7/2004 | Estes et al. |
| 6,783,712 B2 | 8/2004 | Slivka et al. |
| 6,827,743 B2 | 12/2004 | Eisermann et al. |
| 6,830,575 B2 | 12/2004 | Stenzel et al. |
| 6,841,111 B2 | 1/2005 | Rickner et al. |
| 6,843,799 B2 | 1/2005 | Bartlett |
| 6,852,825 B2 | 2/2005 | Lendlein et al. |

(56) References Cited

U.S. PATENT DOCUMENTS

| | | | |
|---|---|---|---|
| 6,869,445 B1 | 3/2005 | Johnson | |
| 6,881,766 B2 | 4/2005 | Hain | |
| 6,902,584 B2 | 6/2005 | Kwan et al. | |
| 6,908,466 B1 | 6/2005 | Bonutti et al. | |
| 6,916,321 B2 | 7/2005 | TehHuisen et al. | |
| 6,923,986 B2* | 8/2005 | Pathak et al. | 424/486 |
| 6,974,862 B2 | 12/2005 | Ringeisen et al. | |
| 7,012,106 B2 | 3/2006 | Yuan et al. | |
| 7,033,603 B2 | 4/2006 | Nelson et al. | |
| 7,045,589 B2* | 5/2006 | Heller et al. | 528/403 |
| 7,192,443 B2 | 3/2007 | Solem et al. | |
| 7,208,550 B2 | 4/2007 | Mather et al. | |
| 7,214,765 B2 | 5/2007 | Ringeisen et al. | |
| 7,261,716 B2 | 8/2007 | Strobel et al. | |
| 7,261,734 B2 | 8/2007 | Gellman et al. | |
| 7,268,205 B2 | 9/2007 | Williams et al. | |
| 7,270,813 B2 | 9/2007 | Shimp et al. | |
| 7,285,087 B2 | 10/2007 | Moaddeb et al. | |
| 7,285,130 B2 | 10/2007 | Austin | |
| 7,314,480 B2 | 1/2008 | Eidenschink et al. | |
| 7,335,375 B2 | 2/2008 | Li et al. | |
| 7,378,144 B2 | 5/2008 | DeMeo et al. | |
| 7,455,674 B2 | 11/2008 | Rose | |
| 7,524,891 B2 | 4/2009 | Rose | |
| 2001/0012940 A1 | 8/2001 | Tunc | |
| 2001/0018614 A1 | 8/2001 | Bianchi | |
| 2002/0022588 A1 | 2/2002 | Wilkie et al. | |
| 2002/0029041 A1 | 3/2002 | Hover et al. | |
| 2002/0029043 A1 | 3/2002 | Ahrens et al. | |
| 2002/0071822 A1 | 6/2002 | Uhrich | |
| 2002/0082362 A1* | 6/2002 | Brocchini et al. | 525/461 |
| 2002/0120348 A1 | 8/2002 | Melican et al. | |
| 2002/0123751 A1 | 9/2002 | Fallin | |
| 2002/0138154 A1 | 9/2002 | Li et al. | |
| 2002/0150775 A1 | 10/2002 | Ishikawa et al. | |
| 2002/0160032 A1 | 10/2002 | Long et al. | |
| 2003/0045941 A1 | 3/2003 | Lewallen | |
| 2003/0055198 A1 | 3/2003 | Langer et al. | |
| 2003/0104031 A1 | 6/2003 | Dumont et al. | |
| 2003/0114937 A1 | 6/2003 | Leatherbury et al. | |
| 2003/0120280 A1 | 6/2003 | Roller et al. | |
| 2003/0125745 A1 | 7/2003 | Tseng et al. | |
| 2003/0130742 A1 | 7/2003 | Connelly et al. | |
| 2003/0153971 A1 | 8/2003 | Chandrasekaran | |
| 2003/0153972 A1 | 8/2003 | Helmus | |
| 2003/0180344 A1 | 9/2003 | Wise et al. | |
| 2003/0236573 A1 | 12/2003 | Evans et al. | |
| 2004/0002770 A1 | 1/2004 | King et al. | |
| 2004/0015187 A1 | 1/2004 | Lendlein et al. | |
| 2004/0019386 A1 | 1/2004 | Ferree | |
| 2004/0030342 A1 | 2/2004 | Trieu et al. | |
| 2004/0052992 A1 | 3/2004 | Boone et al. | |
| 2004/0054372 A1 | 3/2004 | Corden et al. | |
| 2004/0096506 A1* | 5/2004 | Heller et al. | 424/486 |
| 2004/0106734 A1 | 6/2004 | Rose | |
| 2004/0109823 A1 | 6/2004 | Kaplan | |
| 2004/0110285 A1 | 6/2004 | Lendlein et al. | |
| 2004/0115239 A1 | 6/2004 | Shastri et al. | |
| 2004/0131681 A1 | 7/2004 | Ambrose et al. | |
| 2004/0143221 A1 | 7/2004 | Shadduck | |
| 2004/0153075 A1 | 8/2004 | Roger | |
| 2004/0156878 A1 | 8/2004 | Rezania et al. | |
| 2004/0172118 A1 | 9/2004 | Gibson | |
| 2004/0193154 A1 | 9/2004 | Leatherbury et al. | |
| 2004/0241203 A1 | 12/2004 | Shakesheff et al. | |
| 2004/0242722 A1 | 12/2004 | Rose | |
| 2004/0254639 A1 | 12/2004 | Li et al. | |
| 2004/0258732 A1 | 12/2004 | Shikinami | |
| 2004/0259972 A1 | 12/2004 | Ringeisen et al. | |
| 2004/0260398 A1 | 12/2004 | Kelman | |
| 2004/0265385 A1 | 12/2004 | West | |
| 2004/0267263 A1 | 12/2004 | May | |
| 2005/0008672 A1 | 1/2005 | Winterbottom et al. | |
| 2005/0013793 A1 | 1/2005 | Beckman et al. | |
| 2005/0019404 A1 | 1/2005 | Sung et al. | |
| 2005/0033295 A1 | 2/2005 | Wisnewski | |
| 2005/0043751 A1 | 2/2005 | Phan et al. | |
| 2005/0043752 A1 | 2/2005 | Phan et al. | |
| 2005/0070928 A1 | 3/2005 | Heino et al. | |
| 2005/0080483 A1 | 4/2005 | Solem et al. | |
| 2005/0080489 A1 | 4/2005 | Estes et al. | |
| 2005/0085313 A1 | 4/2005 | Nishitani | |
| 2005/0085812 A1 | 4/2005 | Sherman et al. | |
| 2005/0090861 A1 | 4/2005 | Porter | |
| 2005/0107886 A1 | 5/2005 | Crabtree et al. | |
| 2005/0123582 A1 | 6/2005 | Sung et al. | |
| 2005/0125051 A1 | 6/2005 | Eidenschink et al. | |
| 2005/0136764 A1 | 6/2005 | Sherman et al. | |
| 2005/0137611 A1 | 6/2005 | Escudero et al. | |
| 2005/0137715 A1 | 6/2005 | Phan et al. | |
| 2005/0159812 A1 | 7/2005 | Dinger, III et al. | |
| 2005/0165128 A1 | 7/2005 | Cohn et al. | |
| 2005/0177144 A1 | 8/2005 | Phan et al. | |
| 2005/0177245 A1 | 8/2005 | Leatherbury et al. | |
| 2005/0182411 A1 | 8/2005 | DeMeo et al. | |
| 2005/0182428 A1 | 8/2005 | Bearinger et al. | |
| 2005/0187602 A1 | 8/2005 | Eidenschink | |
| 2005/0197422 A1 | 9/2005 | Mayadunne et al. | |
| 2005/0208094 A1 | 9/2005 | Armitage et al. | |
| 2005/0209705 A1 | 9/2005 | Niederauer et al. | |
| 2005/0240281 A1 | 10/2005 | Slivka et al. | |
| 2005/0273106 A1 | 12/2005 | Oepen | |
| 2006/0051394 A1 | 3/2006 | Moore et al. | |
| 2006/0067973 A1 | 3/2006 | Schachter | |
| 2006/0121084 A1 | 6/2006 | Borden et al. | |
| 2006/0121087 A1 | 6/2006 | Williams et al. | |
| 2006/0136071 A1 | 6/2006 | Maspero et al. | |
| 2006/0149248 A1 | 7/2006 | Schlienger et al. | |
| 2006/0177480 A1 | 8/2006 | Sung et al. | |
| 2006/0178748 A1 | 8/2006 | Dinger, III et al. | |
| 2006/0188546 A1 | 8/2006 | Giroux | |
| 2006/0188547 A1 | 8/2006 | Bezwada | |
| 2006/0200150 A1 | 9/2006 | Ilomaki et al. | |
| 2006/0247610 A1 | 11/2006 | Lanphere et al. | |
| 2006/0263335 A1 | 11/2006 | France et al. | |
| 2006/0264948 A1 | 11/2006 | Williams | |
| 2006/0293749 A1 | 12/2006 | Hudgins et al. | |
| 2007/0005094 A1 | 1/2007 | Eaton et al. | |
| 2007/0014831 A1 | 1/2007 | Sung et al. | |
| 2007/0041950 A1 | 2/2007 | Leatherbury et al. | |
| 2007/0043376 A1 | 2/2007 | Leatherbury et al. | |
| 2007/0043433 A1 | 2/2007 | Chandrasekaran | |
| 2007/0048383 A1 | 3/2007 | Helmus | |
| 2007/0050018 A1 | 3/2007 | Wainwright | |
| 2007/0065652 A1 | 3/2007 | Liebschner | |
| 2007/0067043 A1 | 3/2007 | Dericks | |
| 2007/0100449 A1 | 5/2007 | O'Neil et al. | |
| 2007/0128154 A1 | 6/2007 | Hadba et al. | |
| 2007/0134305 A1 | 6/2007 | Zilberman | |
| 2007/0141111 A1 | 6/2007 | Suokas et al. | |
| 2007/0156251 A1 | 7/2007 | Karmon | |
| 2007/0162019 A1 | 7/2007 | Burns et al. | |
| 2007/0182041 A1 | 8/2007 | Rizk et al. | |
| 2007/0191963 A1 | 8/2007 | Winterbottom et al. | |
| 2007/0240281 A1 | 10/2007 | Slivka et al. | |
| 2007/0260324 A1 | 11/2007 | Joshi et al. | |
| 2007/0265622 A1 | 11/2007 | Aeschlimann et al. | |
| 2007/0270852 A1 | 11/2007 | Tormala et al. | |
| 2007/0276366 A1 | 11/2007 | Gaines, Jr. | |
| 2007/0280983 A1 | 12/2007 | Strickler et al. | |
| 2007/0299151 A1 | 12/2007 | Guelcher et al. | |
| 2007/0299156 A1 | 12/2007 | Brown | |
| 2007/0299449 A1 | 12/2007 | Allinniemi et al. | |
| 2008/0015578 A1 | 1/2008 | Erickson et al. | |
| 2008/0045627 A1 | 2/2008 | Rose | |
| 2008/0077140 A1 | 3/2008 | Osman | |
| 2008/0085297 A1 | 4/2008 | Dave et al. | |
| 2008/0086199 A1 | 4/2008 | Dave et al. | |
| 2008/0154368 A1 | 6/2008 | Justis et al. | |
| 2008/0154373 A1 | 6/2008 | Protopsaltis et al. | |
| 2008/0200638 A1 | 8/2008 | Redepenning | |
| 2008/0206297 A1 | 8/2008 | Roeder et al. | |
| 2008/0234754 A1 | 9/2008 | McCarthy et al. | |
| 2008/0234762 A1 | 9/2008 | Forstein et al. | |

(56) References Cited

U.S. PATENT DOCUMENTS

| | | |
|---|---|---|
| 2008/0241211 A1 | 10/2008 | Han et al. |
| 2008/0249633 A1 | 10/2008 | Wu |
| 2008/0262613 A1 | 10/2008 | Gogolewski |
| 2008/0305144 A1 | 12/2008 | Brown et al. |
| 2009/0048145 A1 | 2/2009 | Hellerbrand et al. |
| 2009/0093888 A1 | 4/2009 | Dawson et al. |
| 2009/0099600 A1 | 4/2009 | Moore et al. |
| 2009/0149856 A1 | 6/2009 | Paakinaho et al. |
| 2009/0171064 A1 | 7/2009 | Arimura et al. |
| 2009/0204116 A1 | 8/2009 | Shalaby et al. |
| 2009/0270923 A1 | 10/2009 | Tormala et al. |
| 2009/0274742 A1 | 11/2009 | Brown |

FOREIGN PATENT DOCUMENTS

| | | |
|---|---|---|
| DE | 2817778 | 11/1978 |
| DE | 2947985 | 9/1981 |
| DE | 39 36 188 A1 | 5/1990 |
| DE | 42 26 465 A1 | 2/1993 |
| DE | 42 20 216 C1 | 1/1994 |
| EP | 0 204 931 B2 | 12/1986 |
| EP | 0299004 | 1/1989 |
| EP | 0 321 389 A1 | 6/1989 |
| EP | 326426 A2 | 8/1989 |
| EP | 0 401 844 B1 | 12/1990 |
| EP | 0 439 892 A2 | 8/1991 |
| EP | 475077 B1 | 3/1992 |
| EP | 0590656 | 4/1994 |
| EP | 0 595 956 | 5/1994 |
| EP | 326426 B1 | 12/1994 |
| EP | 0 635 274 A2 | 1/1995 |
| EP | 0 531 487 B1 | 1/1996 |
| EP | 0 711 534 A1 | 5/1996 |
| EP | 747072 A2 | 12/1996 |
| EP | 0751165 A | 6/1997 |
| EP | 0 803 521 A1 | 10/1997 |
| EP | 0 805 175 A1 | 11/1997 |
| EP | 0 806 283 A2 | 11/1997 |
| EP | 1009448 B1 | 6/2000 |
| EP | 1 056 487 B1 | 12/2000 |
| EP | 1086711 A1 | 3/2001 |
| EP | 1 136 510 | 9/2001 |
| EP | 1142597 A1 | 10/2001 |
| EP | 1 093 774 B1 | 6/2002 |
| EP | 1216717 A1 | 6/2002 |
| EP | 1277482 A2 | 1/2003 |
| EP | 0 815 809 B1 | 3/2004 |
| EP | 1284756 B1 | 9/2004 |
| FR | 2707477 A1 | 1/1995 |
| GB | 807589 | 1/1959 |
| GB | 2215209 A | 9/1989 |
| GB | 2319479 | 5/1998 |
| JP | 2169612 | 6/1990 |
| JP | 8196617 | 8/1996 |
| JP | 9040761 | 2/1997 |
| JP | 9095606 | 4/1997 |
| JP | 9221539 | 8/1997 |
| JP | 9234241 | 9/1997 |
| JP | 9272790 | 10/1997 |
| JP | 10176039 | 6/1998 |
| JP | 10309313 | 11/1998 |
| JP | 11209595 | 8/1999 |
| JP | 3503045 | 3/2004 |
| KR | 141988 B1 | 6/1998 |
| WO | WO 84/04311 | 11/1984 |
| WO | WO 90/03768 | 4/1990 |
| WO | WO 93/01773 | 2/1993 |
| WO | WO 95/34331 A1 | 12/1995 |
| WO | WO 97/05193 A1 | 2/1997 |
| WO | 9725936 A1 | 7/1997 |
| WO | 9736555 A1 | 10/1997 |
| WO | WO 98/26814 A1 | 6/1998 |
| WO | 9830141 A2 | 7/1998 |
| WO | 9847445 A1 | 10/1998 |
| WO | 9911296 A2 | 3/1999 |
| WO | WO 99/11297 A2 | 3/1999 |
| WO | WO 99/22770 | 5/1999 |
| WO | WO 00/01426 | 1/2000 |
| WO | WO 01/46501 | 6/2001 |
| WO | WO 01/96105 A2 | 12/2001 |
| WO | WO 02/00137 | 1/2002 |
| WO | 0234310 A2 | 5/2002 |
| WO | WO 0234159 | 5/2002 |
| WO | WO 02/076725 | 10/2002 |
| WO | WO 03/004071 | 1/2003 |
| WO | WO 03/064531 | 8/2003 |
| WO | WO 03/064531 A1 | 8/2003 |
| WO | WO 2004/011054 | 2/2004 |
| WO | WO 2004/071356 A2 | 8/2004 |
| WO | 2004110313 A1 | 12/2004 |
| WO | WO 2005/014718 A1 | 2/2005 |
| WO | 2005028534 A1 | 3/2005 |
| WO | 2005046470 A1 | 5/2005 |
| WO | WO 2005/085313 A1 | 9/2005 |
| WO | 2005112804 A1 | 12/2005 |
| WO | WO 2006/053936 | 5/2006 |
| WO | WO 2006/064025 | 8/2006 |
| WO | 2006108114 A2 | 10/2006 |
| WO | 2006116129 A2 | 11/2006 |
| WO | WO2006114483 | 11/2006 |
| WO | WO 2007/010092 A | 1/2007 |
| WO | 2007021593 A2 | 2/2007 |
| WO | WO 2007/020430 | 2/2007 |
| WO | WO 2007/020432 | 2/2007 |
| WO | 2007023296 A1 | 3/2007 |
| WO | WO 2007/024492 A2 | 3/2007 |
| WO | WO 2007/065074 A2 | 6/2007 |
| WO | WO 2007/084609 A2 | 7/2007 |
| WO | WO 2007/086832 A2 | 8/2007 |
| WO | 2007111808 A2 | 10/2007 |
| WO | WO 2007/117499 A2 | 10/2007 |
| WO | WO2008001633 | 1/2008 |
| WO | WO 2008116591 A2 | 3/2008 |
| WO | WO 2008044011 A2 | 4/2008 |
| WO | WO2008067531 | 6/2008 |
| WO | WO 2008089172 A2 | 7/2008 |
| WO | WO 2008098019 A2 | 8/2008 |
| WO | WO 2008101932 A2 | 8/2008 |
| WO | WO 2008112912 A2 | 9/2008 |
| WO | WO 2008131197 A1 | 10/2008 |
| WO | WO 2008134264 A1 | 11/2008 |

OTHER PUBLICATIONS

Andriano, et al., 'Processing and characterization of absorbable polylactide polymers for use in surgical implants,' *Journal of Applied Biomaterials*, 5(2):133-140 (1994).

Asano, et al., 'In vivo characteristics of low molecular weight copoly(D,L-lactic acid) formulations with controlled release of LH-RH agonist,' *Biomaterials*, 10(8):569-573 (1989).

Barca, et al., 'Resorbable poly-L-lactic acid mini-staples for the fixation of Akin osteotomies,' *The Journal of Foot and Ankle Surgery*, 36(2):106-111 (1997).

Bertrand, et al., Biocompatbility Aspects of New Stent Technology, *JACC*, 32(3):562-571 (1998).

Celikkaya, et al., 'Poly(DL-lactide)/Poly(ethylene glycol) Copolymer Particles. I. Preparation and Characterization,' *Journal of Applied Polymer Science*, 61:1439-1446 (1996).

Frenger, 'Biomedical Uses of Shape Memory Polymers,' *Biomed. Sci. Instrum.*, 29:47-50 (1993).

Fukuzaki, et al., Synthesis of copoly(D,L-Lactic acid) with relatively low molecular weight and in vitro degradation, Japan Atomic Energy Research Institute, Gunma, Jpn, European Polymer Journal, 25(10):1019-1026 (1989).

Giardino, et al., 'Experimental evaluation of a resorbable intramedullary plug for cemented total hip replacement,' *Biomaterials*, 18(13):907-913 (1997).

Gautier, et al., 'Poly($\alpha$-hydroxyacids) for application in the spinal cord: Resorbability and biocompatibility with adult rate Schwann cells and spinal cord,' *Journal of Biomedical Materials Research*, 42(4):642-654 (1998).

(56) References Cited

OTHER PUBLICATIONS

Haers, et al., 'Biodegradable polyactide plates and screws in orthognathic surgery,' *Journal of Cranio-Maxillofacial Surgery*, 26(2):87-91 (1998).
Hyon, et al., 'Effects of residual monomer on the degradation of DL-lactide polymer,' Hyon, Jamshidi & Ikada, *Polymer International*, 46:196-202 (1998).
Kaitian, et al., 'Poly(D,L-Lactic Acid) Homopolymers: Synthesis and Characterization,' *Turkish Journal of Chemistry*, 20:43-53 (1996).
Kister, et al., 'Effects of morphology, conformation and configuration on the IR and Raman spectra of various poly(lactic acid)s,' *Polymer*, 39(2): 267-273 (1998).
Koelling, et al., 'In vitro real-time aging and characterization of poly(L/D-lactic acid),' *Proceedings of the 1997 16th Southern Biomedical Engineering Conference* (Cat. No. 97th8270), pp. 197-201.
Kontio, et al., 'Fibrous wound repair associated with biodegradable poly-L/D-lactide copolymers implants: study of the expression of tenascin and cellular fibronectin,' *Journal of Materials Science—Materials in Medicine*, 9:10:603-609 (1998).
Kricheldorf, et al., 'Polyactones: 32. High-molecular weight polylactides by ring-opening polymerization with dibutylmagnesium or butylmagnesium chloride,' *Polymer*, 36(15):2995-3003 (1995).
Losken, et al., 'Memory of DL-polylactic acid biodegradable plates,' *Ann. Plast. Surg.*, 32(6):606-611 (1994).
MacDonald, et al., 'Enzymatic degradability of poly(lactide): Effects of chain stereochemistry and material crystallinity,' *Macromolecules*, 29(23):7356-7361 (1996).
Mainil-Varlet, et al., 'Effect of in vivo and in vitro degradation on molecular and mechanical properties of various low-molecular weight polylactides,' *Journal of Biomedical Materials Research*, 36(3):360-380 (1997).
Matsumura, et al., 'Novel ring opening polymerization of lactide by lipase,' *Macromol. Symp.*, 130:285-304 (1998).
Morita, et al., 'Intravitreous delivery of dexamethasone sodium m-sulfobenzoate from poly(DL-lactic acid) implants,' *Biological & Pharmaceutical Bulletin*, 21(2):188-190 (1998).
Okihara, et al., Crystal structure of stereocomplex of poly(L-lactide) and poly(D-lactide), *Journal of Macromolecular Science—Physics*, B30(1-2):119-140 (1991).
Penning, et al., 'Preparation and properties of absorbable fibres from L-lactide copolymers,' *Polymer*, 34(5):942-951 (1993).
Pitt, et al., 'Modification of the rates of chain cleavage of poly(ε-caprolactone) and related polyesters in the solid state,' *Journal of Controlled Release*, 4:283-292 (1987).
Rak, et al., 'The preparation and characterization of poly(DL-lactic acid) for use as a biodegradable drug carrier,' Liverpool Polytech., Liverpool, UK, *Pharmaceutica Acta Helvetiae*, 60:(5-6):162-169 (1985).
Ristic, et al., 'An investigation of synthesis and degradation of poly(D,L-lactide) and controlled release of albumin from biodegradable poly(D,L-lactide) cylinders,' ICheaP-2, the second Italian conference on chemical and process engineering, Florence, pp. 559-563 (1995).
Schliephake, et al., 'Reconstruction of the mandible by prefabricated autogenous bone grafts,' *Int. J. Oral Maxillofac. Surg.*, 26:244-252 (1997).
Stahelin, et al., 'Clinical degradation and biocompatibility of different bioabsorbable interference screws: a report of six cases,' *Arthroscopy: The Journal of Arthroscopic & Related Surgery*, 13(2):238-244 (1997).
Steendam, et al., 'The role of elastic relaxation in drug delivery from poly(DL-lactic acid) based tablets. A shape memory phenomenon,' *Proceedings of the International Symposium on Controlled Release of Bioactive Materials*, 25:128-129 (1998).
Stevels, et al., 'Blends van blok copolymeren die een poly(L-lactide) of poly(D-lactide) blok bevatten,' Biomedical Science and Engineering Meeting, pp. 107-110 (1994).

Tagil, "Thesis—The morselized and impacted bone graft animal experiments on proteins, impaction and load," *Acta Orthop. Scand. Suppl.*, 290:1-40 (2000).
Temenoff and Mikos, "Injectable biodegradable materials for orthopedic tissue engineering," *Biomaterials*, 21:2405-2412 (2000).
Tschakaloff, et al., 'Degradation kinetics of biodegradable DL-polyactic acid biodegradable implants depending on the site of implantation,' *International Journal of Oral and Maxillofacial Surgery*, 23(6 Pt2 ):443-445 (1994).
Tsuji, et al., Stereocomplex formation between enantiomeric polylactic acid). VIII. Complex fibers spun from mixed solution of poly(D-lactic acid) and poly(L-lactic acid), *Journal of Applied Polymer Science*, 51(2):337-344 (1994).
Zegzula, et al., 'Bone Formation with Use of rhBMP-2 (Recombinant Human Bone Morphogenetic Protein-2,' *The Journal of Bone and Joint Surgery*, 79:1778-1790 (1997).
Zhang, Biodegradable lactide polymers: synthesis, degradation, and controlled drug release properties (drug release), Queen's University at Kingston, Canada, vol. 55/01-B of Dissertation Abstracts International, p. i-xv, 1-179 (Oct. 1993).
Structure and Properties of Orientated Polymers, Ed. I. M. Ward, Department of Physics, University of Leads, England, a Halsted Press Book, John Wiley & Sons, New York-Toronto (1975) Table of Contents.
Pitto, et al., "Comparison of Fixation of the Femoral Component without Cement and Fixation with Use of a Bone-Vacuum Cementing Technique for the Prevention of Fat Embolism During Total Hip Arthroplasty," *J. Bone Joint Surg.*, 81-A(6):831-843 (1999).
Okuzaki, et al., Mechanical Properties and Structure of the Zone-Drawn Poly(L-lactic acid) Fibers, *Journal of Polymer Science, Part B, Polymer Physics*, 37:991-996 (1999).
Oriented Polymer Materials, Edited by Stoyko Fakirov, published by Huthig & Wepf Verlag Zug, Heidelberg, Oxford CT/USA, Table of Contents pp. v, viii, ix-xix (1996).
Gupta, et al., Poly(lactic acid) fiber: An overview Progress in Polymer Science, Pergamon Press, Oxford, GB, 32(4):455-482 (2007).
Daniels, et al., 'Mechanical properties of biodegradable polymers and composites proposed for internal fixation of bone,' *J. Applied Biomaterials*, 1:57-78 (1990).
Dauner, et al. 'Resorbable continuous-fiber reinforced polymers for osteosynthesis,' *J. Materials Science Materials in Medicine*, 9:173-179 (1998).
Eling, et al., 'Biodegradable Materials of Poly(L-Lactic Acid): 1. Melt-Spun and Solution-Spun Fibres,' *Polymer*, 23:1587-1593 (1982).
Fambri, et al., 'Biodegradable fibres of poly(l-lactic acid) produced by melt spinning,' *Polymer*, 38:79-85 (1997).
Gogolewsji, et al., 'Resorbable materials of poly(L-lactide). II Fibers spun from solutions of poly(L-lactide) in good solvents,' *J. Appl. Polymer Sci.*, 28:1045-1061 (1983).
J. West, J. Hubbell, Bioactive Polymers, *Synthetic Biodegradable Polymer Scaffolds*, Chapter 5, pp. 83-95, Anthony Atala and David J. Mooney, Editors; Joseph P. Vacanti and Robert Langer, Associate Editors, Birkhauser (1997).
D. Hull and T. W. Clyne, 'An introduction to composite materials,' Second Edition, Cambridge University Press, Table of Contents, 8 pages.
L. L. Hench, et al., 'Bioactive materials: The potential for tissue regeneration,' *J. Biomed. Materials Research*, 41(4):511-518 (1998).
D. Wheeler, et al., 'Effect of bioactive glass particle size on osseous regeneration of cancellous defects,' *J. Biomed. Materials Research*, 41(4):527-533 (1998).
Patent Abstracts of Japan for Japanese Publication No. 04-114022, published Apr. 15, 1992 (1 page).
Patent Abstracts of Japan for Japanese Publication No. 05-043773, published Feb. 23, 1993 (1page).
Patent Abstracts of Japan for Japanese Publication No. 06-065468, published Mar. 8, 1994 (1page).

* cited by examiner

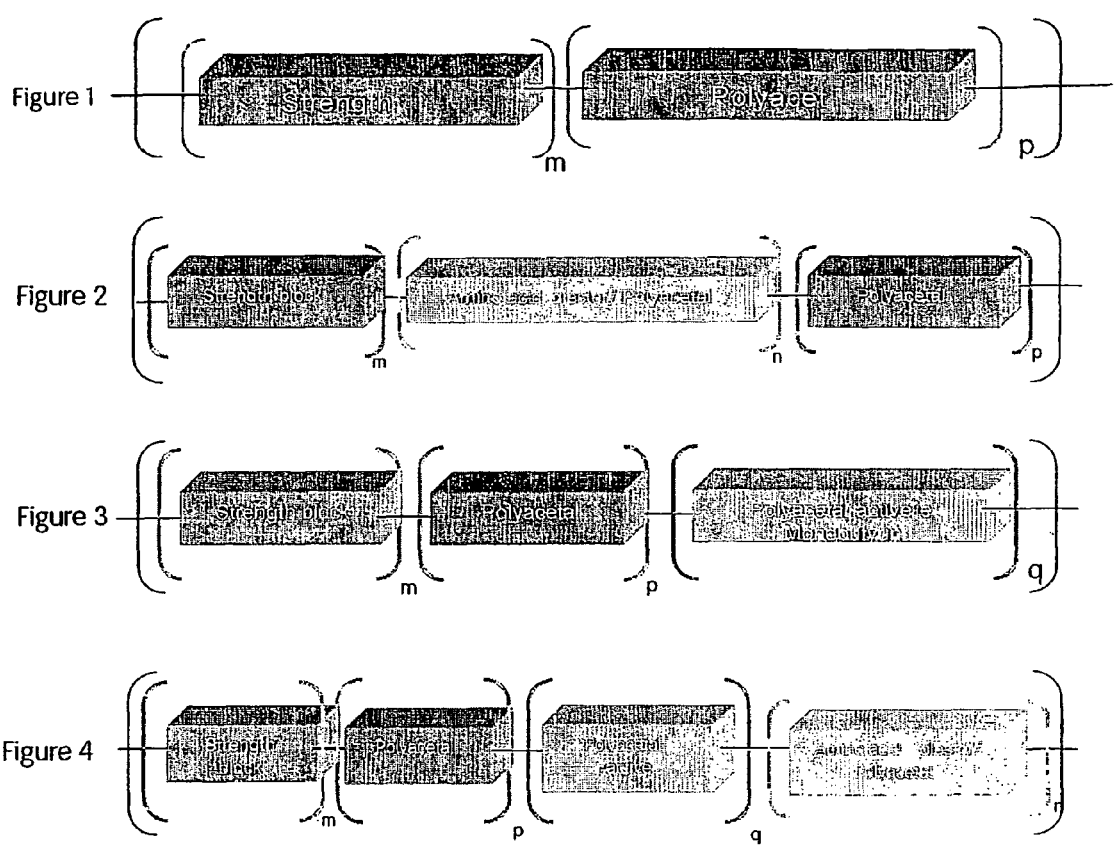

Figure 5. Polyacetal Structure

{[O-POLYMER-O-CH($R_5$)-O$R_4$-OCH($R_5$)-]$_m$-[O-$R_2$-O-CH($R_5$)-O$R_4$-OCH($R_5$)-]$_p$-

[---------------- Strength block -----------------]   [-------Polyacetal block--------------]

-[O-$R_3$-CONH-$R_1$-CO$_2$-$R_2$-O$_2$C-$R_1$-NHCO-$R_3$-O-CH($R_5$)-O$R_4$-OCH($R_5$)-]$_n$-

[---------------amino acid diester/acetal block-----------------------------------]

[O-$R_6$-O-CH($R_5$)-O$R_4$-OCH($R_5$)-]$_q$$_r$

[--------active/polyacetal block----} m = 1-100, n = 0-100, p = 0-100, q = 0-100, r = 1-100

TUNABLE SEGMENTED POLYACETAL

CROSS-REFERENCE TO RELATED APPLICATIONS

This application is the U.S. national phase of International Application No. PCT/GB2004/005445 filed on Dec. 22, 2004, published in English as International Publication No. WO 2005/061617 A1 on Jul. 7, 2005, which claims priority to Great Britain Patent Application No. 03299654.8 filed on Dec. 23, 2003, the contents of which are incorporated herein by reference.

FIELD

The present invention relates to polymer compositions and artifacts made therefrom. In particular the present invention relates to biodegradable polymers having high mechanical strength and their use for the manufacture of load bearing medical devices suitable for implantation within the body.

BACKGROUND

The degradation characteristics of the aliphatic polyesters are not ideal. Polyglycolic acid and copolymers with a high glycolic acid component (e.g. polyglyconate) lose strength rapidly (typically in around 4 weeks). Most healing processes (e.g. fracture repair, bone healing etc) can take longer than this (typically 6 to 12 weeks). Therefore implants made of these polymers do not provide mechanical support over the full duration of healing. For these polymers mass loss generally occurs after about 1-1.5 years. The release of glycolic acid breakdown products has been linked to inflammatory reactions.

In contrast, polymers based on poly(L-lactide) (PLLA) retain their mechanical properties for much longer (typically 6-12 months) which means that they can provide mechanical support throughout the healing process. However, PLLA does not undergo complete mass loss for 3-5 years. This means that the device cannot be replaced by tissue until long after it has ceased to provide any function, if at all. As with PGA, the breakdown products released on degradation are acidic and can lead to an inflammatory response.

One way which has been attempted to create more optimal degradation rates is through the use of copolymers of lactic acid and glycolic acid (PLGA), or copolymers of L-lactic acid and D-lactic acid (PDLLA). The degradation times for these polymers are between those of PLLA and PGA However, these polymers are amorphous and have poorer mechanical properties than PGA and PLLA. Also, like PLLA and PGA they degrade by bulk hydrolysis so that significant mass loss and space generation for tissue ingrowth occurs long after loss of mechanical strength.

A further problem with materials such as PLLA and PGA is that they are brittle and implants made from them can be prone to breaking to the forces exerted on them during insertion. One way that this has been addressed is to copolymerise the PLLA or PGA with a rubber-like polymer such as poly(trimethylene carbonate). This improves the toughness of the polymer but such materials still suffer the same problems of degradation profile as PLLA and PGA.

Another biodegradable polymer which has been used is polycaprolactone (PCL). This polymer melts at around 60° C. so can be delivered to the body in a molten form after which it will set to form an implant in-situ. However, polycaprolactone has a very slow degradation rate so that mass loss in the body takes over 3 years.

It is therefore an objective of the present invention to provide a biodegradable polymer that has optimum strength and degradation characteristics for procedures where biodegradable polymers are implanted.

SUMMARY

According to the present invention there is provided a biodegradable segmented block copolymer comprising polyol residues having a number average molecular weight (Mn) of at least 4000 Daltons connected by acetal linkages.

Said residues are hereinafter referred to as "strength components".

According to a first embodiment of the present invention the acetal linkages comprise polyacetal residues (A schematic representation of polymers in accordance with this embodiment of the invention is shown in FIG. 1 of the accompanying drawings).

In one form of said first embodiment the polyacetal residues may comprise enzyme degradable polyacetal/diamino acid ester blocks (as illustrated FIG. 2 of the accompanying drawings).

Alternatively the polyacetal residues may contain an incorporated bioactive diol (as illustrated in FIG. 3 of the accompanying drawings).

The polyacetal residues may contain both enzyme degradable polyacetal/diamino acid ester blocks and incorporated bioactive diol agent (as illustrated in FIG. 4 of the accompanying drawings).

According to a further embodiment of the present invention the segmented block copolymers of the invention may be blended with other polymeric or ceramic materials The strength components of the present invention are polyols of at least 4000 Daltons or more preferably between 4000 and 20000 daltons. Suitably however the polyol residues may have a molecular weight of at least 5000 Daltons or at least 7500 Daltons or 10000 Daltons.

Aptly the polyol residues will have a molecular weight between 5000 and 17500 Daltons, or between 7500 and 15000 Daltons, or between 10000 and 12500 Daltons.

Suitable polyols may comprise polyesters such as homo- or copolymers of polycaprolactone (PCL), polylactic acid (PLA, L and D forms), polyglycolic acid (PGA) or polydioxanone. Other suitable polyols may comprise degradable aliphatic or aromatic esters, degradable carbonates such as dimethyl trimethylene carbonate (DMTMC), polyamides, polyurethanes and the like.

The amino acid diester/acetal blocks are aptly enzyme degradable blocks linked by acetal links and are based on amino acids. Said blocks can be produced by the reaction of amino acids with amines, acids, alcohols or isocyanates groups to give degradable amino acid containing units which can be converted into the corresponding dihydroxy terminated blocks e.g. a diamino terminated amino acid block can be reacted with caprolactone to yield a dihydroxy terminated enzyme degradable amino acid block.

The biodegradable segmented block copolymers of the present invention may be used with bioactive material. The bioactive agents may be incorporated into, blended with and/or reacted into the biodegradable segmented block copolymer of the present invention.

In other embodiments of the present invention the agent is selected from the group consisting of a growth factor, an antibiotic, a strontium salt, a fluoride salt, a magnesium salt, a sodium salt, a bone morphogenetic factor, a chemotherapeutic agent, a pain killer, a bisphosphonate, a bone growth agent, an angiogenic factor, and combinations thereof. In additional specific embodiments the growth factor is selected from the group consisting of platelet derived growth factor (PDGF), transforming growth factor b (TGF-b), insulin-related growth factor-I (IGF-I), insulin-related growth factor-II (IGF-II), fibroblast growth factor (FGF), beta-2-microglobulin (BDGF II), bone morphogenetic protein (BMP), monobutyrin, butyric acid and combinations thereof. In an additional specific embodiment, the antibiotic is selected from the group consisting of tetracycline hydrochloride, vancomycin, cephalosporins, and aminoglycosides such as tobramycin, gentamicin, and combinations thereof. In another specific embodiment, the factor is selected from the group consisting of proteins of demineralised bone, demineralised bone matrix (DBM), bone protein (BP), bone morphogenetic protein (BMP), osteonectin, osteocalcin, osteogenin, and combinations thereof. In an additional specific embodiment, the agent is selected from the group consisting of cis-platinum, isofamide, methotrexate, doxorubicin hydrochloride, and combinations thereof. In a further specific embodiment, the pain killer is selected from the group consisting of lidocaine hydrochloride, bipivacaine hydrochloride, non-steroidal anti-inflammatory drugs such as ketorolac tromethamine, and combinations thereof.

To promote tissue repair one or several substances can be introduced into the composite bioabsorbable materials of the present invention or impregnated into fabrics or prostheses made from the composite bioabsorbable materials. Exemplary substances include polyeptides such as human growth factors. The term "human growth factor" or "HGF" embraces those materials, known in the literature, which are referred to as such and includes their biologically active, closely related derivatives.

The polyacetal blocks are hydrolytically degradable blocks which may contain aromatic, aliphatic and/or alicyclic groups. The blocks will typically be formed by the reaction of divinyl ethers with alcohols. Typical examples are cyclohexane dimethanol with cyclohexane dimethanol divinyl ether, polylactide diol with cyclohexane dimethanol divinyl ether.

The active polyacetal blocks are based on active alcohols which are linked together by acetal units such that on release these active alcohols cause a physiological effect ie stimulate or inhibit biological processes with the aim of improving healing, suitable examples are monobutryin, hydrocortisone, cholesterol, 1,4 butendol.

The following property enhancements can be obtained through the buffering effect of calcium carbonate (I) Stabilisation of polymer during processing (II) Degradation regulator (II) Modulus improver (IV) Osteoconductive anchoring points. Rate modifying agents may be incorporated into polymers or polymer blends as hereinbefore described by, for example, polymerisation or physical blending. These agents may accelerate degradation, for example acids (e.g. fatty acids, lactic acid), anhydrides (e.g. lauric anhydride) or cyclic esters (e.g. glycolide, lactide). Alternatively the agents may slow down degradation, for example by the use of buffering agents such as bases (e.g. $CaCO_3$, $MgCO_3$).

The use of acids or bases may be used to switch the degradation mechanism from hydrolytic to predominantly enzymatic where the polymer of the invention contains amino acid blocks. For example use of acids will accelerate the degradation of acid sensitive components (i.e. the acetal component) whilst the addition of bases will retard the acetal degradation and thus increase the relative rate of the enzyme degradable amino acid block.

According to the present invention there is further provided a method for improving the modulus of these materials by the incorporation of inorganic (particulate or fibre) and/or polymeric (fibre or particulate) fillers. The addition of inorganic fillers will also be used as an osteogenic promoting material for increasing the binding of osteoclasts and osteoblasts.

The present invention further provides a method for improving the cell binding of these materials by the incorporation of peptide sequences such as RGD, GRGDS, REDV and GREDVY groups. Other groups can be sourced from the literature (ie Synthetic biodegradable polymer scaffolds, Chapter 5 Bioactive polymers, J West, J Hubbell, 1997, ISBN 0-8176-3919-5).

The strength of the polymer of the present invention can be increased through the use of composite technology. The addition of particulates, short fibres and continues fibers can be used either individually or in combination to improve the mechanical properties of the polymers as expected according to composite theory (for example see D Hull and T W Clyne, "An introduction to composite materials", Cambridge university press).

Suitable biocompatible or biodegradable fillers for use may include ceramic materials such as hydroxyapatite (HA) and tri-calciumphosphate (TCP). Biglasses may also be used (eg see L. L. Hench et al, J. Biomed. Materials. Research., Vol 41, 1998, pp 511-518 or D Wheeler et al, J. Biomed. Materials. Research., Vol 41, 1998, pp 527-533). The materials may be processed into either particles or fibers using existing technologies for inclusion into the polymers of this invention.

Additionally polymer fibers may be used to reinforce the polyacetal polymers. These fibers can be made from homopolymers, co-polymers, blends and alloys of the known bioresorbable polymers such as PLLA, PDLA, PGA, PDO, PCL, PTMC, polyanhydrides, polyorthoesters polyacetal and the like.

Additionally fibers could be made from one of the polyacetal compositions disclosed in this invention. These fibers may be incorporated into the polymers using conventional processing techniques such as melting the polymer around fibers via compression moulding or by solvent casting the polymer around the fibers.

The biodegradable segmented block copolymer of the present invention may be injectable to form in situ devices.

In particular embodiments the polyol residue may have a low melting point and may include polyesters having a low melting point (low melting point polyesters) such as polycaprolactone or polybutyladipate. By the term low melting point polyesters we mean polyesters that have a melting point from about 45° C. to about 80° C., suitably the melting point of the low melting point polyesters may also be between 50° C. and 75° C. or 50° C. and 65° C.

Such embodiments of the present invention in which the polyol residue comprises a low melting point polyester would allow the material to be formed/shaped/set in situ and thus can be used in the body. This would allow the present invention to be used as a medical fixation device such as screws and nails.

A method of making a medical fixation device such as screws and nails comprises forming the biodegradable segmented block copolymer of the present invention in situ.

The present invention also provides artifacts formed from the segmented copolymers of the invention. Such artifacts include, but are not limited to screws, suture anchors, plates, drug delivery devices and the like.

The artifacts of the invention may find use in orthopaedic or soft tissue applications. For example said artifacts may include injectable cements for screw augmentation, fracture fixation or improvement of fracture stability, screw/anchor augmentation, ligament fixation, bone reinforcement (for example for use in spine applications) or drug delivery.

The biodegradable segmented block copolymer of the present invention may be used as a coating on a medical device, eg a prosthesis, a suture, a screw, nail or bone plate.

FIG. 5. shows an example of a polyacetal structure in which:
Strength Block=main strength component of polymer
Amino acid diester/acetal block=enzyme degradable and cell compatibility block
Polyacetal block=hydrolytic degradable block
Active/polyacetal=active release block
$R_1$=is an organic residue derived from an amino acid.
$R_2$=is an organic residue derived from an ester or carbamate. and may be derived from an alkyl-, cycloalkyl-, substituted cycloalkyl-, aryl-, substituted aryl-, or alkenyl-alcohol, in which a least one carbon has been replaced at least one C(O)NH— or C(O)O— group
$R_3$=is an organic residue derived from a cyclic ester, cyclic carbonate, hydroxyacid, or amide protected amino acid
$R_4$=is an organic residue derived from an ester or carbamate and may be derived from an alkyl-, cycloalkyl-, substituted cycloalkyl-, aryl-, substituted aryl-, or alkenyl-divinyl ether, in which a least one carbon has been replaced at least one C(O)NH, C(O)NR$_5$ or C(O)O group
$R_5$=is a substituent carried on the divinyl ether and may take the form of a hydrogen, aliphatic alkyl, aromatic or cyclic alkane group.
$R_6$=is an organic residue derived from a biologically active alcohol.
Polymer=is residue of a homopolymer or copolymer diol. Suitable polymeric diols are derived from degradable polyesters, polycarbonates, polyester-carbonates, polyamides, polyamide-esters, polyamide-carbonates or polyurethanes. Examples are polycaprolactone, polylactic acid (D, L or mixture), polyglycolide, polydioxanone, polydimethyl trimethylene carbonate (DMTMC). The polymer blocks suitably have one or more of the following characteristics: (a) glass transition temperature (Tg) above body temperature, (b) crystallinity, (c) hydrogen bonding properties or (d) forms stereo complexes.

The biodegradable segmented block copolymer of the present invention may also contain stabilisers or accelerators.

These may be incorporated into the material to modify the degradation rate of the material. This may be to slow down or speed up the degradation of the material.

By the term accelerator we mean an additive that speeds up or enhances degradation of the material of the present invention. These additives may include acids or derivatives of acids.

The stabiliser(s) or accelerator(s) may be blended into the material of the present invention or indeed may be polymerised into the structure.

Accelerators suitably for use with and/or in the present invention include, but not limited to:

Hexanoic acid, octanoic acid, decanoic acid, lauric acid, myristic acid, crotonic acid, 4-pentenoic acid, 2-hexenoic acid, undecylenic acid, petroselenic acid, oleic acid, erucic acid, 2,4-hexadienoic acid, linoleic acid, linolenic acid, benzoic acid, hydrocinnamic acid, 4-isopropylbenzoic acid, ibuprofen, ricinoleic acid, adipic acid, suberic acid, phthalic acid, 2-bromolauric acid, 2,4-hydroxydodecanoic acid, monobutyrin, 2-hexyldecanoic acid, 2-butyloctanoic acid, 2-ethylhexanoic acid, 2-methylvaleric acid, 3-methylvaleric acid, 4-methylvaleric acid, 2-ethylbutyric acid, trans-beta-hydromuconic acid, isovaleric anhydride, hexanoic anhydride, decanoic anhydride, lauric anhydride, myristic anhydride, 4-pentenoic anhydride, oleic anhydride, linoleic anhydride, benzoic anhydride, poly(azelaic anhydride), 2-octen-1-yl succinic anhydride and phthalic anhydride.

To encourage bone growth into the polymer, it is preferred that the polymer include an osteoconductive filler, e.g., hydroxyapatites (HA), calcium sulfates, tricalcium phosphates, bioactive glasses, aragonite, calcite, and mixtures of these fillers. A suitable level of osteoconductive filler will encourage bone growth without an unacceptable reduction in the deliverability of the polymer. If bone fragments are used without another filler, it is generally preferred that the polymer include from about 0 to 60% bone fragments by weight, more preferably about 20 to 50% weight.

The invention shall be described by way of the following examples and drawings.

BRIEF DESCRIPTION OF THE DRAWINGS

FIG. 1. Shows a schematic representation of an embodiment of the present invention in which the acetal linkages comprise polyacetal residues.

FIG. 2. Shows a schematic representation of an embodiment of the present invention in which the polyacetal residues comprise enzyme degradable polyacetal/diamino acid ester blocks.

FIG. 3. Shows a schematic representation of an embodiment of the present invention in which the polyacetal residues comprise an incorporated bioactive diol.

FIG. 4. Shows a schematic representation of an embodiment of the present invention in which the polyacetal/diamino acid ester blocks and incorporated bioactive agent.

FIG. 5. Shows an example of a polyacetal structure.

DETAILED DESCRIPTION

Examples

Figure 6A:
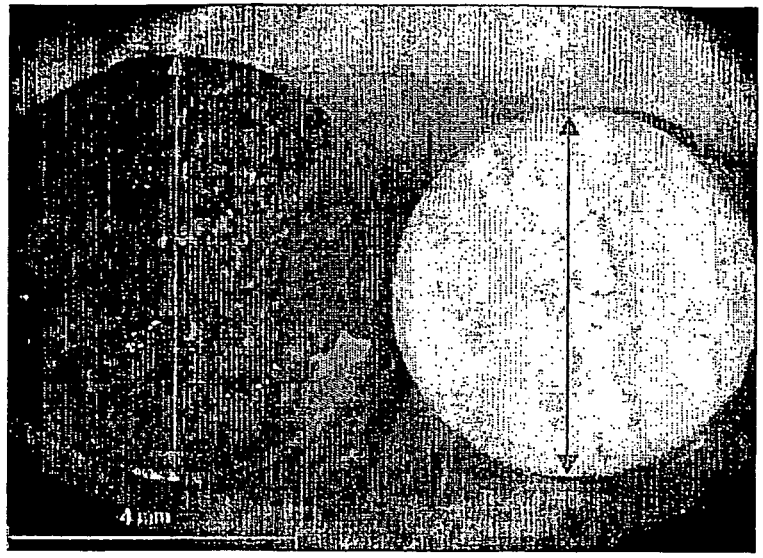
FIG. 6a. Shows reduction in diameter of initial polyacetal after approximately 9 days degradation in buffer from polyacetal (PLA/CHDM/CHDMLVE) degraded in PH 7.4 phosphate buffer solution.

1. Preparation of Polyacetals Containing Different Sized Polycaprolactone Blocks The polycaprolactone diols (PCL) in the amounts shown in Table 1a were respectively placed into 125 ml Wheaton glass vials, together with the corresponding amounts p-toluene sulfonic acid monohydrate (TSA) also shown in Table 1a and 50 ml of anhydrous chloroform. The vials were sealed (silicon stopper/aluminium crimp cap) and the reactants stirred using a magnetic stirrer at room temperature. Cyclohexane dimethanol divinyl ether (CHDMDVE)/anhydrous chlororm (1 ml/10 ml)) solutions was prepared and these were then added in small aliquots over time to each of the vials. Neat CHDMDVE (1 ml and 4 ml) was added to the reactants using low molecular weight PCL diol (Mn=1250 and Mn=580 respectively) in order to reduce the volume of chloroform added to these reactions. Once the reactant mass had become viscous an additional 20 ml of anhydrous chloroform was added to reduced the solution viscosity. These solutions were passed through a $Al_2O_3$/glasswool column and collected in vials containing $CaCO_3$ (2% wt/wt). The $CaCO_3$ was dispersed and the resulting solutions cast onto release paper, molecular weights of the resulting polymers were determined using GPC.

TABLE 1a

Table showing formulations and final molecular weights of Polyacetal (PCL/CHDMDVE) films.

| Molecular weight of polycaprolactone diol | PCL (g) | p-TSA (g) | Total CHDMDVE/total addition time | Mn | Mw |
|---|---|---|---|---|---|
| Mn 10 000 | 10.06 | 0.006 | 0.43 ml/165 min | 48365 | 98805 |
| Mn 4000 | 9.96 | 0.004 | 0.56 ml/178 min | 36290 | 96410 |
| Mn 1250 | 10.33 | 0.008 | 1.60 ml/195 min | 42975 | 107450 |
| Mn 530 | 10.16 | 0.004 | 4.5/248 min | 46895 | 131200 |

Tensile Properties

Above materials were moulded into 1 mm thick flat sheets using a heated press (90 C). Tensile dumbbells were cut and tested on a Zwick 1435 tensile test machine (test speed of 10 mm/min, gauge length=10 mm).

TABLE 1b

Data shows effect of block size on final properties of polyacetal polymer.

| PCL (MWT) | Ultimate tensile strength (MPa) | Modulus (MPa) |
|---|---|---|
| 10 000 | 13.0 | 223 |
| 4000 | 8.05 | 300 |
| 1250 | 2.05 | 9.8 |
| 580 | -too weak | to test |
| PCL only (Control) (Mn = 38 000) | 18.6 | 245 |

TABLE 1c

Effect of block size of PCL on melting and setting temperatures of PCL based polyacetals (all polyacetals have Mn of approx. 40 000).

| PCL block size (Mn) | $T_o$ (° C.) | $T_m$ (° C.) | $\Delta H_f$ (J/g) | $T_c$ (° C.) | Set in water (37 or 20 C.) |
|---|---|---|---|---|---|
| 10 000 | 60.3 | 67.3 | 94.7 | 20.9 | Yes/37 C. |
| 4 000 | 59.5 | 64.4 | 110.7 | 24.2 | Yes/37 C. |
| 1250 | 44.7 | 53.1 | 69.3 | 15.7 | Yes/20 C. |
| 530 | 23.5 | 40.5 | 41.8 | 3.6 | no |
| PCL Control 37 000 | 56.3 | 60.8 | 84.8 | 25.9 | Yes/37 C. |

2. Accelerated Degradation of Polyacetal (PCL (4000)/Vectromer 4060) Using Accelerant Polycaprolactone diol (Mn 4000, 11.7 g) was placed into a 125 ml glass vial. p-Toluene sulfonic acid monohydrate (PTSA, 0.023 g) was added to the vial, followed by 40 ml of anhydrous chloroform. This was stirred using a magnetic stirrer at room temperature. A vectromer 4060 (bis[4-(vinyloxy)butyl]adipate) (1.7 g)/chloroform (15 ml) solution was prepared. This was then added in small aliquots over time until the solution became viscous (10 ml over 1 hr) Anhydrous chloroform (20 ml) was also added to reduce the viscosity of the solution. Sodium hydrogen carbonate solution (1 M, 2 ml) was added and mixed for 15 mins. The polymer was then precipitated and air dried. The final material was dried in a vacuum oven. 3 g of the above polyacetal was dissolved in chloroform (50 ml/anhydrous). Lauric acid (LA, 0.15 g, 5% wt/wt) was added and the solution mixed. The solvent was than removed by casting the solution onto release paper and air dried. The resulting polymer/LA blend was further dried in a vacuum oven (1 hr/room temperature). 2 g of the polymer/LA blend was placed into clean small PTFE pot, heated to 90 C, moulded (5 mins), cooled (room temperature) to yield a small polymer plug (18 mm dia). An accelerated degradation experiment was carried out using this polyacetal (PCL/vectromer 4060) sample, phosphate buffer solution (50 ml) and a sealed plastic vial. The degradation experiment was carried out at 45 C/pH 7.4. The plugs were removed at each time point, wiped dry and a small piece (0.1 g) removed for GPC (chloroform/PS standards) analysis. The plugs were then placed back into the buffer solution and degraded until the following time point was reached.

TABLE 2

Effect of acid accelerant on PCL based polyacetal.

| Material | time/days | Mn (x1000) | Mw (x1000) |
|---|---|---|---|
| Polyacetal (PCl [4K]/ Vectromer 4060) | 0 | 46 | 95 |
|  | 20 | 43 | 93 |
|  | 41 | 40 | 96 |
|  | 115 | 41 | 91 |
| Polyacetal (PCl [4K]/ Vectromer 4060)/5% lauric acid | 0 | 46 | 95 |
|  | 10 | 36 | 78 |
|  | 31 | 27 | 62 |
|  | 105 | 26 | 56 |

3. Preparation of Polyacetals Using PCL (Mn 4000) of Different Block Ratios

Polycaprolactone diol (Mn 4000) and cyclohexane dimethanol(CMDM) were placed into 125 ml glass vials. p-Toluene sulfonic acid monohydrate (pTSA) was added to the vial, followed by 40 ml of anhydrous chloroform. The solutions were stirred using a magnetic stirrer at room temperature. Neat CHDMDVE (3 ml and 2 ml) was added to the respective reactions. Cyclohexane dimethanol divinyl ether (CHDMDVE) (1 ml/10 ml) solutions were prepared, using anhydrous chloroform, and added in small aliquots until the solutions became viscous. 20 ml of anhydrous chloroform was then added, the resulting solution mixed and then passed through a $Al_2O_3$/glasswool column. The resulting solution was collected into separate vials containing $CaCO_3$, mechanical mixed to disperse the $CaCO_3$ and cast onto release paper.

TABLE 3a

Table showing formulations and final molecular weights of Polyacetal (PCL/CHDM/CHDMDVE).

| PCL (g) | CHDM (g) | p-TSA (g) | Total CHDMDVE (ml)/ Total addition time | Mn | Mw |
|---|---|---|---|---|---|
| 5.00 | 3.01 | 0.005 | 4.3 ml/165 min | 48770 | 115900 |
| 7.51 | 1.54 | 0.004 | 2.8 ml/167 min | 47380 | 127700 |

Mechanical Properties

Above materials were moulded into 1 mm thick flat sheets using a heated press (90 C). Tensile dumbbells were cut and tested on a Zwick 1435 tensile test machine (test speed of 10 mm/min, gauge length=10 mm).

TABLE 3b

Data shows effect of block size on final properties of Polyacetal (PCL/CHDM/CHDMDVE) polymer.

| Polymer | Ultimate tensile strength (MPa) | Modulus (MPa) | Mode of failure |
|---|---|---|---|
| PCL only (Mn = 38 000) | 18.6 | 245 | Some breaking below Yield stress, after long yield (Yield then quoted) |
| Polyacetal (PCL (4000)/CHDMDVE) | 8.05 | 300 | Snap @ max stress |
| Polyacetal (PCL (4000)/CHDM/CHDMDVE) (50% PCL) | 4.65 | 24 | Snap @ Max stress (after long pull-out) |

TABLE 3c

Effect of Polyacetal (PCL/CHDM/CHDMDVE). composition on melting and setting properties (all polyacetals have Mn of approx. 40 000).

| Sample No. | $T_o$ (° C.) | $T_m$ (° C.) | $\Delta H_f$ (J/g) | $T_c$ (° C.) |
|---|---|---|---|---|
| Polyacetal (PCL[4000)]CHDM/CHDMDVE) (50% PCL) | 39.6 | 46.4 | 30.1 | — |
| polyacetal (PCL [4000]/CHDM/CHDMDVE) (75% PCL) | 46.9 | 54 | 37.75 | −7.9 |
| Polyacetal blend [polyacetal (PCL [4000]/CHDMDVE) blended with Polyacetal (CHDM/CHDMDVE) (50:50)] | 36.2 | 46.4 | 46.7 | 14 |

Thermoplastic Elastomer

Polyacetal (PCL[4 000)]CHDM/CHDMDVE) (50% PCL) was noted to cold draw to an aligned thermoplastic elastomeric, which stretches (on application of force) and recovers initial dimensions on relaxation of force.

4. Preparation of Polyacetal Using PCL (Mn 4000) and Monobutyrin

PCL diol (Mn 4000) and cyclohexane dimethanol were dried at 60° C. in a vacuum oven. The monobutyrin was dried at room temperature in a vacuum oven. Catalyst (p-TSA) was added to the PCL/CHDM mixtures and monobutyrin was then added. 50 ml of anhydrous chloroform was added and the mixture stirred at room temperature. The reagents were polymerised by the addition of CHDMDVE/anhydrous chloroform (1.0 ml/10 ml) solution, as shown in table 4a, until the polymerisations solutions became viscous. The mixture was diluted with 20 ml of anhydrous chloroform and the solution passed through an $Al_2O_3$/glasswool column. All solutions were collected in separate vials containing $CaCO_3$ (2% wt/wt), mechanically mixed to disperse the $CaCO_3$ and cast on a release paper to yield the following two Polyacetal (PCL/CHDM/Monobutyrin/CHDMDVE).

TABLE 4a

Table showing formulations and final molecular weights of Polyacetal (PCL/CHDM/Monobutyrin/CHDMDVE).

| PCL (g) | CHDM (g) | Monobutyrin (g) | p-TSA (g) | Total CHDMDVE (ml)/ Total time | Mn | Mw | Monobutyrin incorporation (g) |
|---|---|---|---|---|---|---|---|
| 5.08 | 2.09 | 0.946 | 0.003 | 4.5 ml/117 min | 48400 | 140900 | 3.5% |
| 5.02 | 0.9 | 0.4 | 0.0056 | 2.5/60 min | 38980 | 217200 | 2.4% |

TABLE 4b

Table shows the effect of incorporation of monobutyrin on tensile properties of PCL based Polyacetal.

| Composition | Ultimate tensile strength (MPa) | Modulus (MPa) | Mode of failure |
|---|---|---|---|
| Polyacetal (PCL [4000]/CHDMDVE) | 8.05 | 300 | Snap @ max stress |
| Polyacetal (PCL [4000]/CHDM/CHDMDVE) (50% content = PCL) | 4.65 | 24 | Snap @ Max stress (after long pull-out) |
| Polyacetal (PCL [4000]/CHDM/CHDMDVE) acetal blocks + 3.5% monobutyrin (50% content = PCL) | 4.20 | 20.6 | Snap @ max stress |

TABLE 4b-continued

Table shows the effect of incorporation of monobutyrin on tensile properties of PCL based Polyacetal.

| Composition | Ultimate tensile strength (MPa) | Modulus (MPa) | Mode of failure |
|---|---|---|---|
| Polyacetal (PCL [4000]/CHDM/ CHDMDVE) acetal blocks + 2.4% monobutyrin (75% content = PCL) | 5.67 | 33.4 | Slow breaking @ max stress after lower maxima yield & long pull-out |

5. Preparation of Polyacetal(PCL[CHDM/CHDMDVE) Using Bulk Polymerisation Methodologies
Preparation of Catalyst.

5.00 g of PCL diol (Mn 4 000) and 0.0036 g of p-toluene sulphonic acid monohydrate (pTSA) were weighed into a 60 ml glass jar then heated in an oven at 100° C. Once the PCL had melted the contents were mixed thoroughly with a spatula to produce a solution then allowed to cool. The mixture was re-warmed in an oven at 65° C. to produce a clear liquid before use.
Polyacetal (PCL[4000]]CHDM/CHDMDVE) (72% PCL)

7.5 g of PCL diol, 1.06 g CHDM and 1.81 g of CHDMDVE were weighed into a 60 ml glass jar then heated in an oven at 100° C. Once the PCL had melted the contents were mixed with a spatula to produce a homogenous mixture. The jar was then transferred to a 65° C. oven and once it had equilibrated at this temperature, 0.30 g of the catalyst in PCL was added and the contents mixed thoroughly with a magnetic stirrer. The jar was then sealed and returned to the 65° C. oven. Samples were removed from the jar for molecular weight analysis after 4 days of reaction, the results are shown in table 5a.
Polyacetal (CHDM/CHDMDVE)

8.46 g CHDM and 11.53 g of CHDMDVE were weighed into a 60 ml glass jar then heated in an oven at 100° C. Once CHDM had melted the contents were mixed with a spatula to produce a homogenous mixture. The jar was then transferred to a 65° C. oven and once it had equilibrated at this temperature, 0.47 g of the catalyst in PCLdiol was added. The contents were mixed thoroughly with a spatula and the jar sealed and returned to the 65° C. oven. The CHDM and CHDMDVE were found to be immiscible, and were initially removed from the oven, remixed and replaced in the oven several times before being removed and allowed to cool overnight as no increase in viscosity had been observed. The jar was then placed in a water bath, heated at up to 65° C. and stirred with a magnetic stirrer. After half a day of mixing, the materials had reacted to form a clear viscous liquid. The jar was then removed from the water bath and placed back in the 65° C. oven. Molecular weight analysis of the material was carried out after 4 days and after 6 days of reaction, the results are shown in table 5a.

TABLE 5a

Molecular weight distribution of reaction samples

| Sample | Mw | Mn |
|---|---|---|
| 28% polyacetal, 4 days reaction | 54475 | 25900 |
| 100% polyacetal, 6 days reaction | 25760 | 9622 |

6 Polymer Blend

Polyacetal (PCL/CHDMDVE)/Polyacetal (CHDMDVE/CHDM) was prepared by dissolving 2 g of Polyacetal (PCL/CHDMDVE) and Polyacetal (CHDMDVE/CHDM) in chloroform (50 ml). The resulting was cast on release paper. Final molecular weight of blend was Mn=17825, Mw=116800.

7 Applications of In Situ Setting Properties of PCL Based Polyacetals
7a Novel in Situ Forming Anchor Four anchor systems were investigated using a commercial polyethylene terephthalate (PET) Ashway #2 suture. The liquid anchor materials chosen were pure ε-polycaprolactone (PCL), mw=37 000, polyacetal (PCL(Mn=4 000)/CHDM-DVE), and polyacetal (PCL(Mn=4 000)/CHDMDVE)/PCL (Mn=4000) blend. For comparative purposes, a solid OBL RC5 anchor was also selected for study.

Two (Ø2 mm×10 mm) holes, 7 mm apart, were drilled into a block of 20 pcf Sawbone (40×20×20 mm). Each hole was filled with a polymer preheated to 70° C., and a length of suture was placed into the two holes using a hand held tool. The height of the loop formed was fixed at 3.5 mm, which is thought to be wide enough to allow adequate fixation of the supra-spinatus tendon to the bone, and subsequent healing of the rotator cuff injury. For the solid anchor systems, two (Ø5 mm×10 mm) holes were drilled and metal anchors were inserted into these holes using anchor drivers counter sunk to between 0.5 and 1 mm below the surface. Mechanical testing was carried out using an 8511 servo-hydraulic tensile tester fitted with an environmental chamber filled with water heated to 37° C. Each Sawbone block tested was clamped in a g-clamp, and the suture loop, emerging from the block, was attached to the supporting clips which were fed through the holes of the T-piece. This was then held in 30 kN capacity wedge action grips attached to a 1 kN capacity static load cell which was in turn mounted on the actuator of the machine. Pull-out testing was carried out perpendicular to the surface of the Sawbone block at a speed of 32 mm/s until failure occurred, which is either by rupture or by pull-out of the suture device. The load-to failure data were collected on a personal computer and the results were assessed with a force-time diagram. For each anchor system tested, a mean pull-out force was determined from five independent samples.

TABLE 7a

Failure force for in situ formed anchors produced using polyacetals.

| Material for anchor augmentation | Failure force (N) | Variance |
|---|---|---|
| PCL | 98.5 | 17.3 |
| 1L-2 Polyacetal (PCL(Mn = 4 000)/CHDMDVE)/ PCL(Mn = 4000) blend | 88 | 12 |
| 1L-2 polyacetal (PCL(Mn = 4 000)/CHDMDVE)/ PCL(Mn = 4000) blend | 90.2 | 20 |
| Suture | 143 | 0.14 |
| IL-2 RC5 | 132 | 7.7 |

8 Synthesis of PLA Based Polyacetal

8.1 Synthesis of Poly(L) Lactide Diol

Lactide (49.5 g) was placed into 125 ml Wheaton vial and the vial sealed with a silicon stopper and aluminium crimp cap. 1 ml of a tin (ii) dilaurate (0.1 g)/diethylene glycol (5 g) suspension was then added. The vial was placed into an oven (135 C) and heated until all the monomer had melted. The vial was manually agitated during this period. The vial was then heated (135 C) for 69.5 hr to yield a white crystalline solid. The temperature was increased to 165 C and the resulting PLA melt heated for 6 hr. All samples were removed from the oven and cooled to room temperature to yield a white solid. The solid was dissolved in chloroform (80 ml) and precipitated into methanol (2×800 ml). The resulting polymer was collected and dried (air and vacuum oven (5 hr/70 C). The polymer was dried overnight at room temperature/under vacuum (1 mm Hg). The resulting polymer had an Mn=7400/Mw=10804).

8.2 Synthesis of Polyacetal (PLA/CHDM/CHDMDVE)

The following is a general procedure used in the synthesis of polyacetal (PLA/CHDM/CHDMDVE) (50% PLA). The same method, with adjusted reagent ratios, was also used to produce other polyacetals (PLA/CHDM/CHDMDVE) materials with PLA contents between 50-90%, table 8a below.

Poly-l-lactic acid diol (6g, Mn=7400/Mw=10804), CHDM (2.5 g) was placed into a 125 ml glass vial. p-Toluene sulfonic acid monohydrate (3.3 mg) was added to the vial and the contents dried in a vacuum oven (60 C/4 hr). The vial was then sealed (silicon stopper/aluminium crimp lid) and 50 ml of anhydrous chloroform was added. This was stirred using a magnetic stirrer at room temperature. The PLA diol was polymerised with (cis/trans) cyclohexane dimethanol divinyl ether (CHDMDVE), 3.3 ml of neat CHDMDVE and 2 ml dilute CHDMDVE/anhydrous chloroform (1 ml/10 ml) solution. The reaction was noted be very viscous. An additional 20 ml of chloroform was added to reduce the solution viscosity. This solution was passed through an $Al_2O_3$/glasswool column and collected into a vial containing $CaCO_3$. The collected solution was mixed using mechanical rollers and cast onto release sheets, properties:—Mn=19 800, Mw=47 600, Tg=−3.2 C & 42 C, Tm=143.2 C.

Tensile test samples were moulded using these Polyacetals (PLA/CHDM/CHDMDVE) polymers and their respective tensile properties determined.

TABLE 8a

Table shows the effect of PLA block content on tensile properties of the Polyacetal(PLA/CHDM/CHDMDVE).

| PLA content (wt %) | Acetal content (Wt %) | Filler Type/Level | Mn (×1000) | Mw (× 1000) | U. Tensile Strength (MPa) | Modulus (MPa) |
|---|---|---|---|---|---|---|
| 50 | 50 | $CaCO_3$/2% | 18 | 75 | 12 | 300 |
| 60 | 40 | $CaCO_3$/4% | 37 | 85 | 16.1 | 177 |
| 70 | 30 | $CaCO_3$/4% | 31.5 | 68 | 20.6 | 260 |
| 87 | 13 | $CaCO_3$/4% | 27 | 61 | 7 | 664 |

9 Degradation of Polyacetal(PLA/CHDM/CHDMDVE)

Figure 6B:
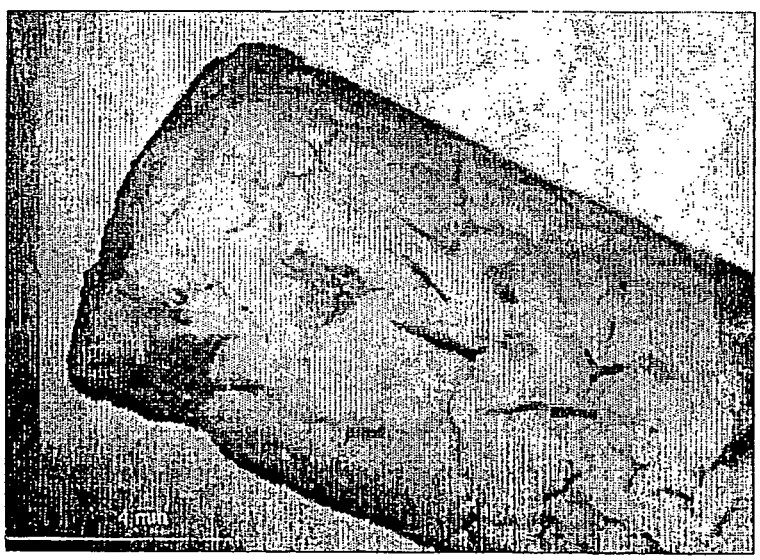
FIG. 6b. Shows effect of degradation on surface of polyacetal.

Polyacetal(PLA CHDM/CHDMDVE) was produced using the following procedure Poly-l-lactic acid diol (4.5 g, Mn=5200/Mw=10800) ), CHDM (2.1 g) was placed into a 125 ml glass vial. p-Toluene sulfonic acid monohydrate (12 mg) was added to the vial and the contents dried in a vacuum oven (100 C/4 hr). The vial was then sealed (silicon stopper/aluminium crimp lid) and anhydrous chloroform (40 ml) added. This was stirred using a magnetic stirrer at room temperature. The PLA diol was polymerised with (cis/trans) cyclohexane dimethanol divinyl ether (CHDMDVE). A CHDMDVE/anhydrous chloroform solution (2.55 g/10 ml) was prepared and aliquots added to the stirred solution over a 2 hr period. A further CHDMDVE/Chloroform (2 g/10 ml) solution was prepared. 9 ml of this solution was added over 2.5 hr period. The reaction became very viscous, an additional 20 ml of chloroform was added to the mixture to reduce the viscosity. The polymer was purified by passing the solution through an $Al_2O_3$/glasswool column and precipitated into methanol. The final polymer was collected and dried (air dried and vacuum oven (60 C/4 hr)). Molecular weight of polymer Mn=35 500/Mw=126 000. Polymer rods (approx. 6.0 mm diameter) were produced by packing a PTFE block, containing a 6.2 mm hole with polymer. This was heated at 170 C until the polymer had become molten. The molten polymer was compressed and cooled to form a soft rod which crystallised on cooling. Small plugs (approx. 10 mm in length) were cut and degraded in both acid (pH 3) and buffer solution (pH 7.4), FIG. 6. The degradation data is given in table 9a below.

TABLE 9a

Data shows change in weight and diameter of degrading polyacetal (PLA/CHDM/CHDMDVE) with time and pH.

| PH of solution | Total deg Time days | Weight (g) | Wt Change | % Wt loss (g) | Diameter/ mm | Diameter change/ mm | % Diameter reduction |
|---|---|---|---|---|---|---|---|
| 3 | 0.0 | 0.2953 | — | 0 | 6.07 | — | 0 |
|  | 0.9 | 0.2950 | −0.0003 | 0.11 | 6.02 | −0.05 | 0.82 |
|  | 3.8 | 0.2669 | −0.0284 | 9.6 | 5.89 | −0.18 | 2.96 |
|  | 4.8 | 0.2484 | −0.0469 | 15.9 | 5.82 | −0.25 | 4.1 |
|  | 6.2 | 0.2265 | −0.0688 | 23.3 | 5.72 | −0.35 | 5.8 |
|  | 8.2 | 0.2084 | −0.087 | 29.4 | 5.61 | −0.46 | 7.6 |
|  | 11.1 | 0.1694 | −0.1259 | 42 | 5.36 | −0.71 | 11.7 |
|  | 13.9 | 0.1471 | −0.1482 | 50.2 | 5.27 | −0.8 | 13.1 |
| 7.4 | 0.0 | 0.2657 | 0 | 0 | 6.08 | 0 | 0 |
|  | 0.9 | 0.2652 | −0.0005 | 0.19 | 5.95 | −0.13 | 2.1 |
|  | 3.8 | 0.2518 | −0.0139 | 5.2 | 5.94 | −0.14 | 2.3 |
|  | 4.8 | 0.2433 | −0.0224 | 8.4 | 5.87 | −0.21 | 3.4 |
|  | 6.2 | 0.2327 | −0.033 | 12.4 | 5.83 | −0.25 | 4.1 |
|  | 8.2 | 0.2236 | −0.0421 | 15.8 | 5.76 | −0.32 | 5.3 |
|  | 11.1 | 0.2033 | −0.0624 | 23.5 | 5.65 | −0.43 | 7.1 |
|  | 13.9 | 0.1882 | −0.0775 | 29.2 | 5.58 | −0.50 | 8.2 |
|  | 19.8 | 0.1710 | −0.0947 | 35.6 | 5.43 | −0.65 | 8.9 |
|  | 23.9 | 0.1644 | −0.1013 | 38.1 | 5.38 | −0.7 | 11.5 |
|  | 27.1 | 0.1595 | −0.1062 | 39.9 | 5.28 | −0.80 | 13.1 |
|  | 31.1 | 0.1552 | −0.1105 | 41.5 | 5.22 | −0.86 | 14.1 |
|  | 33.4 | 0.1518 | −0.1139 | 42.8 | 5.19 | −0.89 | 14.6 |
|  | 39.4 | 0.1427 | −0.123 | 46.3 | 5.12 | −0.96 | 15.8 |
|  | 58.3 | 0.1299 | −0.1358 | 51.1 | 4.99 | −1.09 | 17.9 |
|  | 101.3 | 0.1040 | −0.1617 | 60.8 | — | — | — |

10 Effect of Buffering Agent on Thermal Stability of Polyacetal(PLA/CHDM/CHDMDVE)

Polyacetal (PLA/CHDM/CHDMDVE)/$CaCO_3$ blends were produced by solution blending (PLA/CHDM/CHDMDVE) (3.5 g) with $CaCO_3$ powder (3.5 g) in chloroform (20 ml). The resulting solution was cast to form films and dried (air dried overnight then vacuum oven 80 C). Polymer rods (approx. 9.3 mm diameter) were produced by packing a PTFE block, containing a 9.3 mm hole, with polymer/$CaCO_3$. The mould/polymer was heated to 185 C until the polymer had become molten. The molten polymer was then compressed and cooled. A opaque white rod was formed on cooling.

TABLE 10a

Data shows the effect of temperature on the molecular weight of stabilised and unstabilised polyacetal (PLA/CHDM/CHDMDVE).

| Material | Mn | Mw |
|---|---|---|
| Polyacetal (PLA/CHDM/CHDMDVE) (control) | 13710 | 28350 |
| Polyacetal (PLA/CHDM/CHDMDVE)/Heat 185 C. | 6980.5 | 15155 |
| Polyacetal (PLA/CHDM/CHDMDVE)/CaCO₃/Heat 185 C. | 9149 | 21685 |

11 Effect of $CaCO_3$(Buffer on Degradation of Polyacetal (PLA/CHDM/CHDMDVE)

Polyacetal (PLA/CHDM/CHDMDVE)/Caco₃ Rod was Cut to Give a Plug (9.3 mm diameter×7.55 mm length). The sample was placed into a sealed pot and degraded 37 C/pH 7.4 in phosphate buffer solution.

TABLE 11a

Data shows the effect of $CaCO_3$ on weight and diameter of degrading polyacetal (PLA/CHDM/CHDMDVE) with time.

| Sample Polyacetal (PLA/CHDM/CHDMDVE) | Total degradation Time days | Weight (g) | % Wt change (g) | Diameter/mm | % Diameter change |
|---|---|---|---|---|---|
| Contains 50% (wt/wt) CaCO₃ buffered | 0.0 | 0.7407 | 0 | 9.31 | 0 |
| | 3.7 | 0.7395 | −0.16 | 9.32 | +0.11 |
| | 5.6 | 0.7386 | −0.28 | 9.30 | −0.11 |
| | 11.3 | 0.7371 | −0.48 | 9.285 | −0.27 |
| | 16.3 | 0.7332 | −1.01 | 9.26 | −0.54 |
| | 35.1 | 0.7261 | −1.96 | 9.22 | −0.97 |
| | 80.1 | 0.7149 | −3.48 | 9.11 | −2.14 |
| | 230.1 | 0.6948 | −6.9 | 9.05 | −2.8 |
| No CaCO₃ | 0.0 | 0.2657 | 0 | 6.08 | 0 |
| | 0.9 | 0.2652 | −0.19 | 5.95 | −2.1 |
| | 3.8 | 0.2518 | −5.2 | 5.94 | −2.3 |
| | 4.8 | 0.2433 | −8.4 | 5.87 | −3.4 |
| | 6.2 | 0.2327 | −12.4 | 5.83 | −4.1 |
| | 8.2 | 0.2236 | −15.8 | 5.76 | −5.3 |
| | 11.1 | 0.2033 | −23.5 | 5.65 | −7.1 |
| | 13.9 | 0.1882 | −29.2 | 5.58 | −8.2 |
| | 19.8 | 0.1710 | −35.6 | 5.43 | −8.9 |
| | 23.9 | 0.1644 | −38.1 | 5.38 | −11.5 |
| | 27.1 | 0.1595 | −39.9 | 5.28 | −13.1 |
| | 31.1 | 0.1552 | −41.5 | 5.22 | −14.1 |
| | 33.4 | 0.1518 | −42.8 | 5.19 | −14.6 |
| | 39.4 | 0.1427 | −46.3 | 5.12 | −15.8 |
| | 58.3 | 0.1299 | −51.1 | 4.99 | −17.9 |
| | 101.3 | 0.1040 | −60.8 | — | — |

12 Use of Inorganic Filler to Enhance the Modulus of PLA Based Polyacetals

Polyacetal (PLA/CHDM/CHDMDVE)/CaCO₃ containing 50% hydroxyapatite (HA) was produced by solution blending Polyacetal (PLA/CHDM/CHDMDVE)/(50% Wt PLA)/CaCO₃ with HA particles (Ceramed). The resulting solution was cast and dried. Tensile samples were produced by compression moulding the blend using the Fontijne heated hydraulic press to produce 15 cm round sheets. Tensile samples were produced by cutting dumbbells using the 5 mm short dumbbell cutter and an Atom SE8 hydraulic clicker press.

TABLE 12a

Data shows the effect of filler level on modulus of polyacetal (PLA/CHDM/CHDMDVE) with time.

| PLA content (wt %) | Acetal content (Wt %) | Filler Type/Level | Mn | Mw | U. Tensile Strength (MPa) | Modulus (MPa) |
|---|---|---|---|---|---|---|
| 50 | 50 | CaCO₃ (2%) | 18000 | 75000 | 12 | 300 |
| 50 | 50 | CaCO₃ (2%) HA (50%) | 14000 | 65000 | 12.6 | 900 |

13 Synthesis of Polyacetal (PLA/CHDM/Amino Acid Diester/CHDMDVE)

The reaction path following the scheme below:—

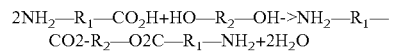
    Step 1

    Step 2

    Step 3 m=1-100, n=0-100, p=0-100, r=1-100

Step 1: Diamino Ester

L-Phenylalanine (16.5 g, 0.1 moles) was reacted with cyclohexane dimethanol (7.2 g, 0.05 moles) and p-toluene sulfonic acid monohydrate (20 g, 0.105 moles). These reagents were heated in 130 ml toluene under reflux using a Dean Stark head in order to collect the water. A volume of 2.6 ml of water was collected. The toluene solvent was removed on a rotary evaporator to leave a crude white powdery product. The white powder was purified by washing with absolute alcohol (3×80 ml) and drying the resulting product to constant weight in a vacuum oven. The product was suspended in 200 ml of deionised water (80 C) and neutralised with potassium carbonate (10 g). Gas($CO_2$) was evolved resulting in the formation of an oil/water emulsion. On cooling to room temp this yielded a light brown solid. The solid was collected, dissolved in chloroform, dried with magnesium sulphate, filtered and the solution reduced on a rotor evaporator to yield a brown-cream solid. Structure of diamino ester was confirmed using $^1$H-NMR and the FT-IR.

Step 2: Diamino Ester/Caprolactone Adduct

Diphenylalanine ester (2.5 g) and caprolactone (2.5 g) were placed into a Wheaton vial (10 ml). The vial was sealed (silicon stopper & aluminium crimp cap) and placed in an extracted oven at 105 C (2 hr) then 150 C (5 hr), the sample was manually agitated during this period. It was noted that the diester melted quickly and became soluble in the caprolactone to yield a yellow product. The sample was reacted for further 14 hrs, removed and cooled to yield a viscous brown liquid. Structure of diamino ester confirmed using $^1$H-NMR and the FT-IR.

Degradation of Diphenylalanineester/Caprolactone Adduct Using Chymotyrpsin

Approximately 1.0 g of diphenylalanine ester/caprolactone adduct was placed into 2 separate polypropylene containers (25 mm×5.5 mm). These were placed into 2 polycarbonate jars (25 ml). Materials were then degraded by exposing the materials to either (I) chymotrypsin solution or (II) Tris buffer solution. These solutions were prepared by:—
(a) Producing a stock enzyme solution containing 0.5 g of Chymotrypsin in 3.366 ml of 1.0 mM HCL. This was used to make a 25 ml enzyme solution having an activity of 500 units/ml by adding Tris Buffer Solution (22.67 ml), 2M $CaCl_2$ Solution (0.675 ml) and stock enzyme solution (1.65 ml) into a polycarbonate pot. 10 ml of this solution was transferred into a 25 ml polycarbonate pot containing a diphenylalanine adduct sample.
(b) The buffer (control) solution was prepared using a similar method. This was then made by adding Tris buffer Solution (22.67 ml), 2M $CaCl_2$ Solution (0.675 ml) and dilute HCl solution (1.65 ml) into a sealed polycarbonate pot. 10 ml of this solution was transferred into a 25 ml polycarbonate pot containing a diphenylalanineester/caprolactone adduct sample.

All samples were incubated at 37 C with mechanical agitation. Samples were removed from there respective solutions, air dried (2 days) and weighted. These samples were further degraded in the respective solutions. The degradation solutions were also changed ever 3 days to ensure a high activity of the enzyme.

TABLE 13a

Enzymatic and hydrolytic degradation of diamino ester/caprolactone block containing 5 units of caprolactone

| Degradation media | Time | Mass loss (%) |
|---|---|---|
| Chymotrypsin (500 units), tris buffer/37 C. | 0 | 0 |
| | 48 | 9.1 |
| | 145 | 26.9 |
| | 193 | 36.5 |
| | 262 | 51.4 |
| | 310 | 58.6 |
| | 363 | 65.7 |
| | 450 | 74.2 |

TABLE 13a-continued

Enzymatic and hydrolytic degradation of diamino ester/caprolactone block containing 5 units of caprolactone

| Degradation media | Time | Mass loss (%) |
|---|---|---|
| Tris buffer/37 C. | 0 | 0 |
| | 48 | −0.86 |
| | 145 | 1.81 |
| | 193 | 3.73 |
| | 262 | 5.8 |
| | 310 | 7.3 |
| | 363 | 8.9 |
| | 450 | 9.8 |

Step 3: PLA Based Polyacetal Containing Diamino Ester/Caprolactone Adduct

Polyacetal(PLA/CHDM/CHDMDVE/phenylalanine ester-caprolactone adduct) was produced using the following procedure: Poly-l-lactic acid diol (4 g, Mn=5200/Mw=10800) and diphenylalanine ester/caprolactone (3.0 g) adducts were placed into a 125 ml glass vial. p-Toluene sulfonic acid monohydrate(16 mg) was added to the vial and the contents dried in a vacuum oven (100 C/4 hr). The vial was then stoppered (silicon stopper/aluminium crimp lid) and 30 ml of anhydrous chloroform was added. This was stirred using a magnetic stirrer at room temperature. The PLA diol was polymerised with (cis/trans) cyclohexane dimethanol divinyl ether (CHDMDVE). A CHDMDVE/anhydrous chloroform solution (2 g/10 ml) was prepared and added in small aliquots. The resulting solution was noted to become cloudy. The solution was then filtered, via a syringe fitted with a 0.45 um nylon filter, into a separated sealed Wheaton vial (125 ml) containing CHDM (1.0 g), magnetic stirrer and p-TSA (10 mg). This formed a clear straw yellow solution. 9 ml of a CHDMDVE/chloroform solution (1.23 g/10 ml chloroform) was added over a 2 hr period. The resulting viscous solution was purified by passing the solution through an $Al_2O_3$/glasswool column, precipitating into methanol and dried to remove residual solvent. The polymer structure was confirmed using FTIR and NMR. Polymer rods (approx. 6.0 mm diameter) were produced by packing a PTFE block, containing a 6.2 mm hole, with polymer. The resulting mould was heated at 180 for 10 mins until the polymer had become molten. The molten polymer was then compressed and cooled to form a soft rod which crystallised on cooling.

TABLE 13b

Data shows the effect of heat on polyacetal (PLA/CHDM/CHDMDVE/phenylalanine ester-caprolactone) during the moulding process.

| Polymer | Mn | Mw |
|---|---|---|
| Initial polymer | 42560 | 111150 |
| Heated to form plug | 30555 | 78300 |

14. Degradation PLA Based Polyacetal Containing Diamino Ester/Caprolactone Adduct Polyacetal (PLA/CHDM/CHDMDVE/phenylalanine ester-caprolactone adduct) were produced using the above method. Polymer plugs were cut from the polyacetal rod using a diamond saw. The enzymatic degradation of these materials was then evaluated by degrading the polymers plugs at 37 C/pH7.8/in 10 ml of enzymatic or buffer solutions. The protocols for the preparation of the enzyme and buffer solution are given in example 13.

TABLE 14a

Enzymatic and hydrolytic degradation of Polyacetal
(PLA/CHDM/CHDMDVE/phenylalanine ester-caprolactone adduct)

| Sample Polyacetal(PLA/ CHDM/CHDMDVE/ phenylalanine ester-caprolactone adduct) | Total deg Time days | Weight (g) | % Wt change (g) | Diameter/ mm | % Diameter change |
|---|---|---|---|---|---|
| Buffered solution | 0 | 0.1392 | 0 | 5.86 | 0 |
|  | 2 | 0.1396 | +0.26 | 5.86 | 0 |
|  | 9 | 0.1379 | −0.95 | 5.85 | −0.2 |
|  | 19.8 | 0.128 | −7.2 | 5.84 | −0.34 |
|  | 23.8 | 0.1261 | −9.4 | 5.84 | −0.34 |
| Enzyme solution | 0 | 0.1750 | 0 | 5.94 | 0 |
|  | 1.16 | 0.1755 | +0.27 | 5.95 | +0.16 |
|  | 9 | 0.1741 | −0.52 | 5.91 | −0.50 |
|  | 19.8 | 0.1409 | −19.5 | 5.76 | −3.03 |
|  | 23.8 | 0.1280 | −26.8 | 5.59 | −5.9 |

15. Polyacetal(PLA/CHDM/CHDMDVE/Tryptophan Diester-CL Adduct)/$CaCO_3$ Blend

Polyacetal(PLA/CHDM/CHDMDVE/Tryptophan diester-CL adduct) was prepared using the above methodology. Polymer structure was confirmed using FTIR and NMR and the molecular weight via GPC (Mn=23 900 and Mw=152 600). 3 g of Polyacetal(PLA/CHDM/CHDMDVE/Tryptophan diester-CL adduct) placed in glass vial containing $CaCO_3$ (3 g) powder. Dichloromethane (10 ml) was added and the solution agitated until all the polymer had dissolved. The solution was cast and dried to remove residual solvent. A rod was moulded by packing the polymer blend into a PTFE mould (9. mm diameter hole), heated (160 C) and cooled to yield a polymer rod.

TABLE 15a

Data shows the effect of heat on polyacetal
(PLA/CHDM/CHDMDVE/Tryptophan ester-caprolactone adduct)
during the moulding process.

| Polymer | Mn | Mw |
|---|---|---|
| Initial polymer | 23 900 | 152 600 |
| Heated to form plug (180 C/10 min) | 17 000 | 131 000 |
| Polymer/$CaCO_3$ heated to form plug (180 C/10 min) | 17 000 | 205 000 |

16. Cell Adhesion

Figure 7:
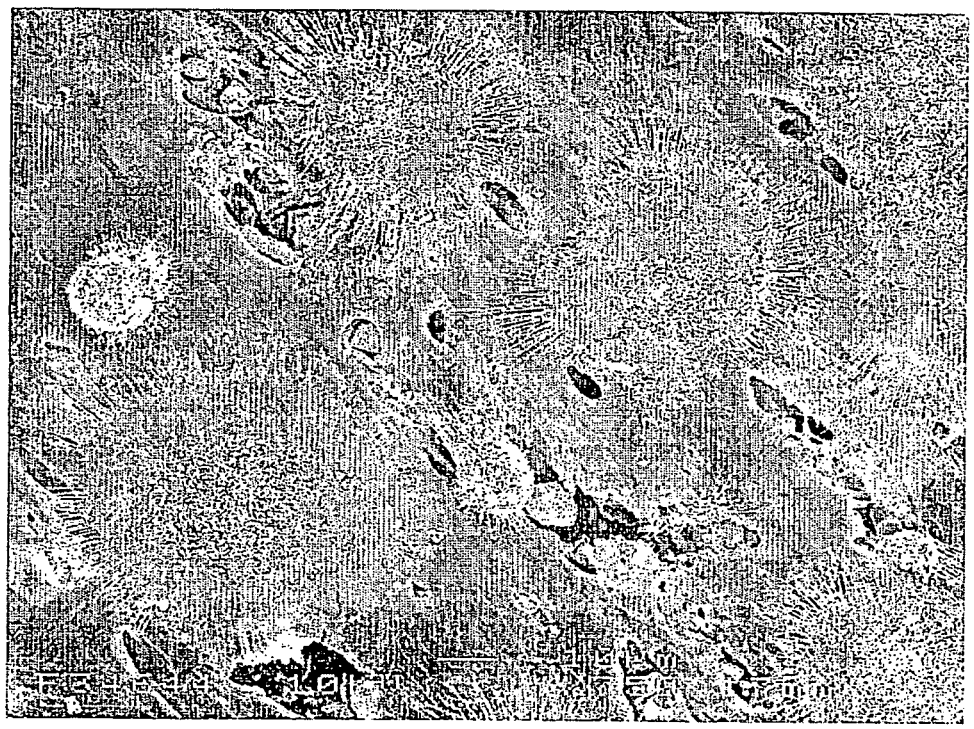
FIG. 7. Shows osteoclast adhesion onto polyacetal (PLA/CHDM/CHDMDVE/Trytophan diester-caprolactone) $CaCO_3$ surface FIG. 8a. Shows preosteoblastic MC3T3-E1 cultured around discs of polyacetal (PLA/CHDM/CHDMDVE/Trytophan diester-caprolactone) $CaCO_3$ indicated that the materials did not exert a gross cytotoxic effect on cells: from bulk material cytotoxicity testing of the materials using WST test.

Cell binding was found to be dependent upon the chemical composition of the Polyacetal. Human peripheral blood derived osteoclasts were differentiated in situ on discs of polyacetal test materials. Polyacetal-(tryptophan diester/PLA), polyacetal-(tryptophan diester/PLA)/$CaCO_3$, polyacetal-(PLA/CHDM/CHDMVE), polyacetal-(PLA/CHDM/CHDMVE)/$CaCO_3$ and control materials were tested over the 4 week culture period during which the osteoclast progenitor cells differentiated into mature osteoclasts, FIG. 7. After 6 and 19 days in culture, cells were observed attached to the control materials and polyacetal-(tryptophan diester/PLA)/$CaCO_3$. Further cells were attached to the polyacetal-(tryptophan diester/PLA). There were also no cells attached to the polyacetal-(PLA/CH DM/CHDMVE) or polyacetal-(PLA/CH DM/CHDMVE)/$CaCO_3$ after 12 days in culture. These effects do not appear to be caused by the materials having cytotoxicity issues.

Figure 8A:
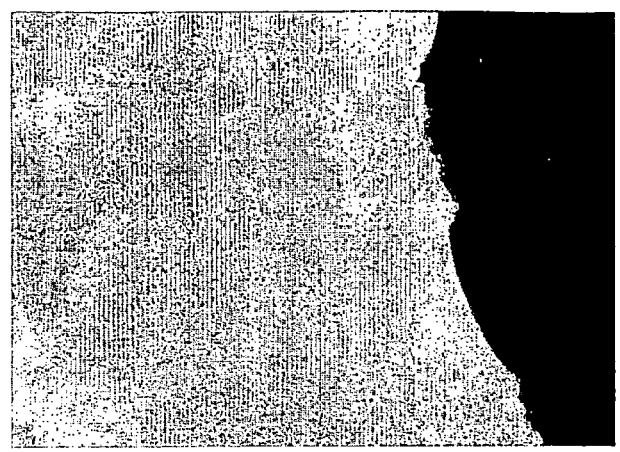
FIG. 8b. Shows all viability (as a function of absorbance) with a range of filled and unfilled PLA based polyacetals, from bulk material cytotoxicity testing of the materials using WST test.
Figure 8B:
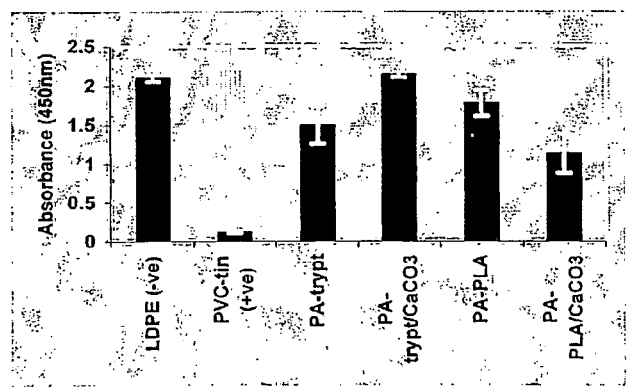
Figure 9:
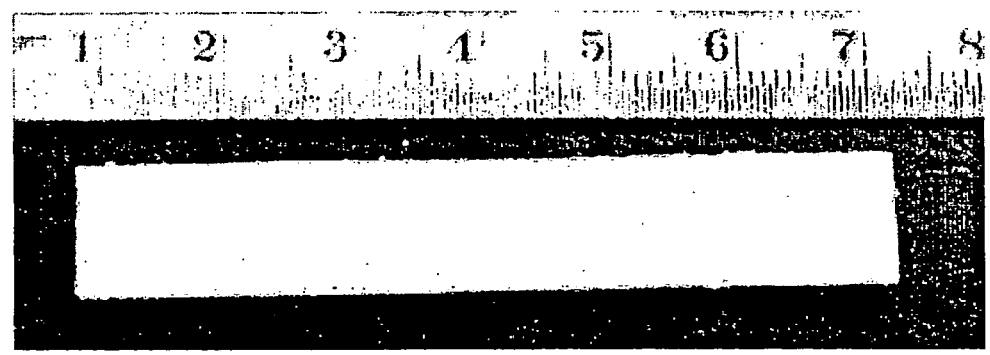
FIG. 9. Shows a typical composite bar according to the present invention.
Figure 10:
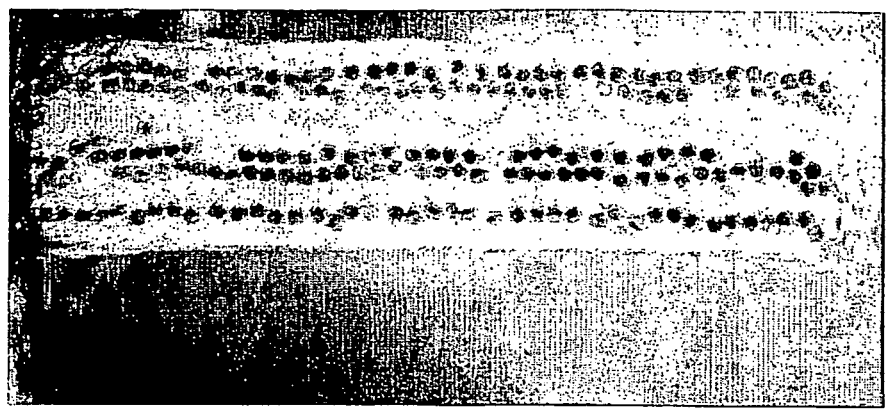
FIG. 10. Shows a section through a typical composite bar according to the present invention.

Bulk material cytotoxicity testing of the materials, using preosteoblastic MC3T3-E1, cultured around discs of the materials indicated that the materials did not exert a gross cytotoxic effect on cells, FIG. 8. The lack of cells attached to the polyacetal-(tryptophan diester/PLA), polyacetal-(PLA/CHDM/CHDMVE) and polyacetal-(PLA/CHDM/CHDMVE)/$CaCO_3$ can be related to their degradation rate in vitro and suggests that the cells were lost due to erosion of the discs surface. Where as cells were still present on the polyacetal-(tryptophan diester/PLA)/$CaCO_3$ discs which coincided with this material having the lowest degradation rate in vitro.

Cell viability experiments were also carried out using a WST method. Polyacetal samples were degraded in acid (pH 3), 37 C for 2 wk. The solution were then neutralised with $Na_2CO_3$ Various concentrations of degradation solutions were prepared by using a serial dilution method, using culture medium. MC3T3-E1 (osteoblast-like) were then cultured for 24 h with test solutions. Cell viability was assayed. Control solutions were produced from (I)LDPE conditioned medium and (II)PVC/Tin conditioned medium. The cytotoxicity of both glycolic and lactic acid were measured as controls. The highest tolerated concentration of glycolic acid showing >90% cell viability was 0.1 mg/ml whilst the highest tolerated concentration of lactic acid showing >90% cell viability 0.5 mg/ml.

TABLE 16a

WST Cell viability experiment data showing cell viability with
degradation products generated from the accelerated degradation of
polyacetal(PLA/CHDM/CHDMVE/Phenylalanine diester-caprolactone) and
Polyacetal(PLA/CHDM/CHDMVE)

| Polyacetal(PLA/CHDM/CHDMVE/Phenylalanine diester-caprolactone) | | | | | | |
|---|---|---|---|---|---|---|
| Concentration (mg/ml) | 0.5015 | 0.2507 | 0.1253 | 0.0627 | 0.0313 | 0.0157 |
| Cell viability (Mean cell viability expressed as % of medium only control) | 106 | 103 | 89.5 | 90.3 | 97.1 | 97.6 |
| Polyacetal(PLA/CHDM/CHDMVE) | | | | | | |
| Concentration (mg/ml) | 3.153 | 1.576 | 0.788 | 0.394 | 0.197 | 0.098 |
| Cell viability (Mean cell viability expressed as % of medium only control) | 0 | 87.8 | 107.4 | 100.5 | 97.1 | 97.6 |

17. Production of Composite Bars

Materials.

PLLA-co-PA (50:50)+4% w/w $CaCO_3$

High-strength PGA Fibre.

Method.

1. Compression Moulding of PLLA-co-PA into Sheets.

10 g of polymer was compression moulded between two sheets of PTFE impregnated glass cloth for 1 minute at 135° C., 50 kN force. The resulting sheet of polymer was then cut up and re-moulded under the same conditions to reduce the number of bubbles.

The moulded sheet were vacuum dried at 50° C., approx. 0.1 mbar for 2 hours.

2. Preparation of the Fibre.

The fibre was wound around a metal sheet lined with PTFE impregnated glass cloth to produce a tightly wound spiral approx 6.5 cm across. 0.5 mm thick shims were attached to the plate, placed up against both sides of the spiral on both sides of the plate to stabilise it during moulding.

The fibre and plate were then heated between sheets of PTFE impregnated glass cloth in the press for 2 minutes at 135° C. The plate was then removed from the press and before it had time to cool sheets of PLLA-co-PA were placed over the PGA fibre on both sides of the plate. The plate was the returned to the press for 30 seconds under low pressure to allow the PLLA-co-PA to melt, then 30 seconds at 50 kN pressure to force the polymer into the fibre. The press was then crash cooled and the plate removed to yield two sheets of composite containing a single layer of fibre (one from each side of the plate). The composite sheet was then cut to produce 1.0×7.0 cm strips with the fibre-orientated parallel to the long side, 3. Production of Composite.

An aluminium block (1×4×12 cm) with a slot (0.3×1×12 cm) was used as a mould.

The bottom of the mould was lined with a strip of PTFE impregnated glass cloth and the mould heated to 135° C. in a press. Once the mould had warmed up the press was opened and 5 strips of composite sheet were added one at a time, after each new sheet was added a roller was used to remove any bubbles between the sheets.

The mould was then covered with a sheet of PTFE impregnated glass cloth and pressed with 50 kN force for 1 minute, the press was then crash cooled and the mould removed. The mould was then cooled with dry ice and the composite bars removed by tapping the mould. The composite bars were then dried immediately in a vacuum oven at room temperature approx. 0.1 mbar to remove condensation resulting from the freezing process. After drying the ends of the bar were trimmed to make them parallel, a typical composite bar, and a cross section though the bar are shown in FIGS. 1 & 2.

Four bars were manufactured and submitted for tensile testing. After tensile testing one half of the bar was submitted for GPC to determine the molecular weight distribution. 1 cm lengths were cut from the two of the bars and used to determine the fibre content in duplicate. This was done by weighing and measuring the sample, then washing the matrix from the fibres using chloroform. The remaining fibres were then dried and weighed.

Results.

The molecular weight distribution of the starting polymer, matrix of the individual bars and the PGA fibre are summarised in table 2.

TABLE 2

Molecular weight distribution of composite matrix and fibre.

| Sample | Sample number | Mw | Mn | Pd |
|---|---|---|---|---|
| Matrix polymer | ET238-2250-3-13S | 103950 | 24475 | 4.28 |
| Composite 1 matrix. | ET238-2250-13-3A | 76860 | 15840 | 4.85 |
| Composite 2 matrix. | ET238-2250-13-3B | 83105 | 17725 | 4.69 |
| Composite 3 matrix. | ET238-2250-13-3C | 91385 | 18545 | 4.93 |
| Composite 4 matrix. | ET238-2250-13-3D | 94515 | 19760 | 4.78 |
| Mean | | 86466 | 17968 | 4.81 |
| Composite 1 fibre. | ET238-2250-13-3A | 89730 | 38910 | 2.31 |
| Composite 2 fibre. | ET238-2250-13-3B | 89825 | 37405 | 2.40 |
| Composite 3 fibre. | ET238-2250-13-3C | 86605 | 33635 | 2.57 |
| Composite 4 fibre. | ET238-2250-13-3D | 86970 | 41885 | 2.08 |
| Mean | | 88283 | 37959 | 2.34 |

The mechanical properties of the composite bars are summarised in table 3.

TABLE 3 mechanical properties of composite bars.

| Sample | $\sigma_F$ (MPa) | $E_F$ (MPa) | $\epsilon_F$ (%) |
|---|---|---|---|
| ET238-2250-13-3A | 182.4 | 398.9 | 35.3 |
| ET238-2250-13-3B | 169.3 | 396.0 | 39.9 |
| ET238-2250-13-3C | 169.6 | 554.7 | 31.4 |
| ET238-2250-13-3D | 169.1 | 509.0 | 42.5 |
| Mean (SD) | 172.6 (5.7) | 464.7 (69.1) | 37.3 (4.3) |

The weight composition of the composite was measured and volume composition calculated assuming a PGA fibre density of 1.53 $gcm^{-3}$. The density of the matrix polymer was also calculated these results are summarised in table 4.

TABLE 4

Composite composition.

| | Fibre | | Matrix |
|---|---|---|---|
| sample | (% w/w) | (% v/v) | (gcm-3) |
| 3A | 30.6 | 25.7 | 1.20 |
| 3A | 31.2 | 25.8 | 1.17 |
| 3B | 30.3 | 23.9 | 1.10 |
| 3B | 28.7 | 23.4 | 1.16 |
| Mean | 30.2 | 24.7 | 1.16 |

Degradation Experiments of PCL Based Polyacetals

Polycaprolctone(PCL) based acetals used in this study were produced using the methodologies described in this patent. The polycaprolactone-co-polyacetal copolymers used in this study were synthesised from PCL diol (Mn=10 k) and contained approximately 95% (PCL-co-PA(CHDMDVE)) and 50% (PCL-co-PA(CHDM/CHDMDVE)) PCL. Lauric anhydride (LAH) (2% wt/wt) was solution blended into the above copolymers, cast on opposite sheet and dried. Polycaprolactone-co-polyacetal polymers and the corresponding lauric anhydride blends were then packed into PCL syringes and melt moulded at 105 C to form rods. Cylindrical plugs were cut from the rods to standard dimensions (10 mm long, and 4.6 mm in diameter). The mass of each material was kept fairly constant ensuring that direct comparisons could be made between each sample. Each sample was placed in a vial, containing 30 mls of Phosphate Buffer Solution, (PBS). Two degradation profiles were set up to investigate the effect of mass loss and molecular weight loss in novel PCL based materials. The first aging profile was conducted at physiological conditions (37° C., PBS) and the second study at accelerated conditions (45° C., PBS). In both cases, samples were immersed in 30 mls of PBS, and the buffer solution was not replaced at any time point preventing any periodic fluid analysis. "Clip on" tops were used in the study to help minimise any evaporation that might have taken place from the vials during storage. Samples were degraded for 10 weeks, removed and evaluated (MWT and mass loss). A total of 3 replicates per material per time point were used for this study. Initially, the dry weight of each sample was recorded. Each sample was terminally discarded at each time point. At each time point the PBS was drained from the vials and the "wet weight" of the samples were recorded after a small amount of hand drying was undertaken to remove the excess PBS. Subsequently, the samples were dried using a vacuum pump to remove the residual fluid, and hence obtain a "dry weight". This technique was used to monitor the mass loss of the samples over time. Gel permeation chromatography (GPC) was carried out on the terminal samples to determine changes in molecular weight. The collected data was compared to the initial time point, and an appropriate analysis undertake PLA-co-PA (CHDM/CHDMDVE and PLA-co-PA (CHDM/CHDMDVE)/HA (40% wt/wt) sheets were cut into small sections and ground in a cryomill to produce powder suitable for feeding into a Rondol 12 mm single screw extruder. The materials were then extruded into rods under the following conditions:—

(i) Polyacetal (PLA-co-PA (CHDM/CHDMDVE) Rods
Screw speed=90 units
Barrel temp=135° C.
Die temp=140° C.

Melt was extruded into hot PTFE blocks (130° C.) containing 6.4 mm holes, approximately 50 mm long. The polymer melt extrudate filled 7 blocks. The blocks were cooled in a freezer to aid removal of the polymer rods.

(II) Polyacetal (PLA-co-PA (CHDM/CHDMDVE)/HA Rods
Screw speed=90 units
Barrel temp=170° C.
Die temp=170° C.

Melt was extruded into hot PTFE blocks (130° C.) containing 6.4 mm holes, approximately 50 long. The polymer melt extrudate filled 10 blocks. The blocks were cooled in a freeze to aid removal of the polymer rods.

| Change in Molecular Weight and Mass during degradation at 37 C. in PBS | | | | | | |
|---|---|---|---|---|---|---|
| Sample | Mw (T = 0 Wk) | Mn (T = 0 wk) | Mw (T = 0 wk) | Mn (T = 10 wk) | % Change in mass (T = 0 Wk) | % Change in mass (T = 10 wk) |
| PCL-co-PA(CHDM/CHDMDVE) | 88797 | 32683 | 83727 | 26767 | 0 | −0.21 |
| PCL-co-PA/CHDM/CHDMDVE)/ LAH 2% | 93657 | 31297 | 65547 | 21087 | 0 | −1.3 |
| PCL-co-PA(CHDMDVE) | 195133 | 76013 | 175733 | 64257 | 0 | −0.45 |
| PCL-co-PA (CHDMDVE)/ LAH 2% | 190933 | 78927 | 100007 | 39343 | 0 | −1.95 |

18. In Vivo Evaluation
Production of Polymer Plug

Polylactide(PLLA) based polyacetals used in this study were produced using the methodologies described in example 8. The PLA-co-Polyacetal copolymers were synthesized from PLLA diol (Mn=7.5 K) and contained approximately 50% PLLA.

The PLA-co-PA (CHDM/CHDMDVE)/HA (40% wt/wt) blend was produced by solution blending polyacetal(PLA/CHDM/CHDMDVE) copolymer and hydroxyapatite (HA, previously dried at 170 C./15 hr) in sealed Wheaton vials (125 ml), casting onto an opposite release paper and air-dried.

Polymer plugs were produced by cutting the rods, on a Buehler Isomet 2000 saw, to yield plugs of 11 mm in length. These were then ground on a Buehler Metaserv polisher to produce plugs tapered at one end. All rods were washed in absolute alcohol and air-dried. All samples were placed into separate view packs and batched. Samples were weighted, measured and ETO sterilisation. All samples were analysed before implanting (Table XX—Molecular weight and. Thermal properties)

| Material | Form | Mn | Mw | Tg (° C.) 1st heat | Tm (° C.) 1st heat | ΔH (J/g) 1st heat |
|---|---|---|---|---|---|---|
| PLA-co-PA (CHDM/CHDMDVE | Extruded Plug | 20775 | 47685 | −7.6/39.9 | 144.0 | 20.7 |
| PLA-co-PA (CHDM/CHDMDVE | Plug sterilised (ETO) | 21145 | 49490 | −4.3/39.1 | 142.9 | 20.2 |
| PLA-co-PA (CHDM/CHDMDVE)/HA | Extruded Plug | 27795 | 68395 | −5.0/42.6 | 143.2 | 14.0 |
| PLA-co-PA (CHDM/CHDMDVE)/HA | Plug sterilised (ETO) | 25880 | 64750 | −5.9/39.4 | 140 | 10.7 |

An in vivo study was carried out using a clinically relevant bone site. The polymer plugs were implanted, harvested after 12 months, declassified and stained using a standard H&E stain. Both polymer plugs showed signs of surface cracking, polymer erosion and ossification at the surface of the implant. Total reduction of surface area of the implants was calculated to be 17.5% (±0.6) and 21.5% (±0.4) for the PLA-co-PA (CHDM/CHDMDVE) and PLA-co-PA (CHDM/CHDM-DVE)/HA respectively.

What is claimed is:

1. A biodegradable segmented block copolymer comprising strength blocks each comprising repeat units, each repeat unit comprising a polymer polyol residue, wherein the polymer polyol residues each have a molecular weight of at least 4000 Daltons, wherein the strength blocks are connected by acetal linkages, wherein the polymer polyol residues are selected from the group consisting of polyesters, degradable carbonates, and polyamides, and wherein the biodegradable segmented block copolymer is insoluble in physiological conditions.

2. The biodegradable segmented block copolymer of claim 1, wherein the acetal linkages comprise polyacetal residues.

3. The biodegradable segmented block copolymer of claim 2, wherein the polyacetal residues comprise enzyme degradable polyacetal/diamino acid ester blocks.

4. The biodegradable segmented block copolymer of claim 2, wherein the polyacetal residues comprise an incorporated bioactive diol.

5. The biodegradable segmented block copolymer of claim 2, wherein the polyacetal residues comprise enzyme degradable polyacetal/diamino acid ester blocks and incorporated bioactive agent.

6. The biodegradable segmented block copolymer of claim 1, wherein the segmented block copolymer is blended with at least one agent selected from the group consisting of other polymeric, ceramic, and glass material.

7. The biodegradable segmented block copolymer of claim 1, wherein the polymer polyol residues have a molecular weight of at least 5000 Daltons.

8. The biodegradable segmented block copolymer of claim 1, wherein the polymer polyol residues have a molecular weight between 4000 and 20000 Daltons.

9. The biodegradable segmented block copolymer of claim 1, wherein the polymer polyol residues comprise a polyester.

10. The biodegradable segmented block copolymer of claim 9, wherein the polyester is selected from the group consisting of homo-polymers and co-polymers of polycaprolactone (PCL), polylactic acid (PLA, L and D forms), polyglycolic acid (PGA), polydioxanone, aliphatic esters and aromatic esters.

11. The biodegradable segmented block copolymer of claim 1, wherein the polymer polyol residues comprise a degradable carbonate.

12. The biodegradable segmented block copolymer of claim 1, wherein the polymer polyol residues comprise a polyamide.

13. The biodegradable segmented block copolymer of claim 1, wherein the biodegradable segmented block copolymer further comprises a polymer selected from the group consisting of polyglycolic acid (PGA), polycaprolactone (PCL) and polylactic acid (PLA).

14. The biodegradable segmented block copolymer of claim 1, wherein the biodegradable segmented block copolymer further comprises a biocompatible inorganic material.

15. The biodegradable segmented block copolymer of claim 14, wherein the biocompatible inorganic material is selected from the group consisting of calcium carbonate, hydroxyapatite (RA), and tricalcium phosphate (TCP).

16. The biodegradable segmented block copolymer of claim 1, wherein a stabilizer and/or accelerator is blended into and/or polymerized into the biodegradable segmented block copolymer.

17. The biodegradable segmented block copolymer of claim 1, further comprising a biological active agent blended in and/or reacted with the segmented block copolymer.

18. The biodegradable segmented block copolymer of claim 17, wherein said biological active agent is selected from the group consisting of a growth factor, an antibiotic, a strontium salt, a fluoride salt, a magnesium salt, a sodium salt, a bone morphogenetic factor, a chemotherapeutic agent, a pain killer, a bisphosphonate, a bone growth agent, an angiogenic factor, and any combination thereof.

19. The biodegradable segmented block copolymer of claim 18, wherein said biological agent comprises a growth factor and wherein said growth factor is selected from the group consisting of platelet derived growth factor (PDGF), transforming growth factor beta (TGF-beta), insulin-related growth factor-I (IGF-I), insulin-related growth factor-II (IGF-II), fibroblast growth factor (FGF), beta-2-microglobulin (BDGF II), bone morphogenetic protein (BMP), and any combination thereof.

20. The biodegradable segmented block copolymer of claim 18, wherein said biological agent comprises an antibiotic and wherein said antibiotic is selected from the group consisting of tetracycline hydrochloride, vancomycin, cephalosporins, and aminoglycosides such as tobramycin, gentacin, and any combination thereof.

21. The biodegradable segmented block copolymer of claim 18, wherein said biological agent comprises a bone growth agent and wherein said bone growth agent is selected from the group consisting of proteins of demineralised bone, demineralised bone matrix (DBM), bone protein (BO), bone morphogenetic protein (BMP), osteonectin, osteocalcin, osteogenin, and any combination thereof.

22. The biodegradable segmented block copolymer of claim 18, wherein said biological agent comprises a chemotherapeutic agent and wherein said chemotherapeutic agent is selected from the group consisting of cisplatinum, ifosfamide, methotrexate, doxorubicin hydrochloride, and any combination thereof.

23. The biodegradable segmented block copolymer of claim 18, wherein said biological agent comprises a pain killer and wherein said pain killer is selected from the group consisting of lidocaine hydrochloride, bipivacain hydrochloride, non-steroidal anti-inflammatory drugs including ketorolac tromethamine, and any combination thereof.

24. The biodegradable segmented block copolymer of claim 1, wherein the biodegradable segmented block copolymer further comprises a reinforcing material.

25. The biodegradable segmented block copolymer of claim 24, wherein the reinforcing material comprises a polymer filler particulate.

26. The biodegradable segmented block copolymer of claim 24, wherein the reinforcing material comprises a fiber.

27. The biodegradable segmented block copolymer of claim 1, wherein the biodegradable segmented block copolymer forms in whole, or part, a medical device.

28. A medical device comprising the biodegradable segmented block copolymer of claim 1.

29. A method of manufacture of a medical device comprising forming in situ the biodegradable segmented block copolymer of claim 1.

30. The medical device of claim 28, wherein the biodegradable segmented block copolymer comprises a coating on the medical device.

* * * * *